(12) United States Patent
Suda et al.

(10) Patent No.: US 8,906,521 B2
(45) Date of Patent: Dec. 9, 2014

(54) ORGANIC ELECTROLUMINESCENT DEVICE HAVING TRIPTYCENE DERIVATIVE MATERIAL

(75) Inventors: Mitsuru Suda, Kitakyushu (JP); Takahiro Kai, Kitakyushu (JP); Toshihiro Yamamoto, Kitakyushu (JP)

(73) Assignee: Nippon Steel & Sumikin Chemical Co., Ltd., Tokyo (JP)

( * ) Notice: Subject to any disclaimer, the term of this patent is extended or adjusted under 35 U.S.C. 154(b) by 351 days.

(21) Appl. No.: 13/143,263

(22) PCT Filed: Jan. 15, 2010

(86) PCT No.: PCT/JP2010/050391
§ 371 (c)(1),
(2), (4) Date: Jul. 5, 2011

(87) PCT Pub. No.: WO2010/082621
PCT Pub. Date: Jul. 22, 2010

(65) Prior Publication Data
US 2011/0272680 A1  Nov. 10, 2011

(30) Foreign Application Priority Data

Jan. 19, 2009 (JP) .................................. 2009-008796

(51) Int. Cl.
| | | |
|---|---|---|
| *H01L 51/54* | (2006.01) | |
| *C09K 11/06* | (2006.01) | |
| *C07D 209/86* | (2006.01) | |
| *C07D 213/74* | (2006.01) | |
| *C07D 239/48* | (2006.01) | |
| *C07D 403/10* | (2006.01) | |
| *C07D 403/14* | (2006.01) | |
| *C07D 471/14* | (2006.01) | |
| *H01L 51/00* | (2006.01) | |
| *H01L 51/50* | (2006.01) | |

(52) U.S. Cl.
CPC ............ *C07D 209/86* (2013.01); *C07D 213/74* (2013.01); *C07D 239/48* (2013.01); *C07D 403/10* (2013.01); *C07D 403/14* (2013.01); *C07D 471/14* (2013.01); *H01L 51/0072* (2013.01); *H01L 51/5016* (2013.01); *H01L 51/5048* (2013.01); *H01L 51/5096* (2013.01); *Y10S 428/917* (2013.01)
USPC ........... 428/690; 428/917; 313/502; 313/504; 257/40; 257/E51.049

(58) Field of Classification Search
None
See application file for complete search history.

(56) References Cited

U.S. PATENT DOCUMENTS

| | | |
|---|---|---|
| 6,509,110 B1 | 1/2003 | Salbeck et al. |
| 6,605,693 B1 | 8/2003 | Becker et al. |
| 6,649,283 B1 | 11/2003 | Lupo et al. |
| 2003/0017361 A1* | 1/2003 | Thompson et al. ........... 428/690 |
| 2004/0048098 A1 | 3/2004 | Hoffman |
| 2004/0048099 A1 | 3/2004 | Chen et al. |
| 2007/0051944 A1 | 3/2007 | Vestweber et al. |
| 2009/0105488 A1* | 4/2009 | Cheng et al. .................. 548/440 |
| 2009/0273278 A1 | 11/2009 | Lee et al. |

FOREIGN PATENT DOCUMENTS

| | | |
|---|---|---|
| EP | 2141214 A2 | 1/2010 |
| JP | 2001-520255 A | 10/2001 |
| JP | 2002-15871 A | 1/2002 |
| JP | 2002-532846 A | 10/2002 |
| JP | 2002-539286 A | 11/2002 |
| JP | 2004-95554 A | 3/2004 |
| JP | 2007-520875 A | 7/2007 |
| JP | 2009-292807 A | 12/2009 |
| JP | 2010-74111 A | 4/2010 |

OTHER PUBLICATIONS

International Search Report, dated Apr. 13, 2010, issued in PCT/JP2010/050391.
Extended European Search Report, dated May 3, 2012, for European Application No. 10731290.2.

* cited by examiner

*Primary Examiner* — Andrew K Bohaty
(74) *Attorney, Agent, or Firm* — Birch, Stewart, Kolasch & Birch, LLP

(57) ABSTRACT

Disclosed is a useful organic EL device which comprises a phosphorescent light-emitting layer and is endowed with improved luminous efficiency and high driving stability. Also disclosed is a hole-transporting material suitable for use in the phosphorescent light-emitting device. The hole-transporting material is a triptycene derivative which has substituents at the 9- and 10-positions and is substituted with an aromatic group containing at least one diarylamino group (—ArNAr$_2$). The organic EL device contains the triptycene derivative in at least one organic layer selected from the group of a phosphorescent light-emitting layer, a hole-transporting layer, an electron-blocking layer, and an exciton-blocking layer. The diarylamino group (—NAr$_2$) may be fused to form an aromatic heterocyclic group such as a carbazolyl group.

3 Claims, 1 Drawing Sheet

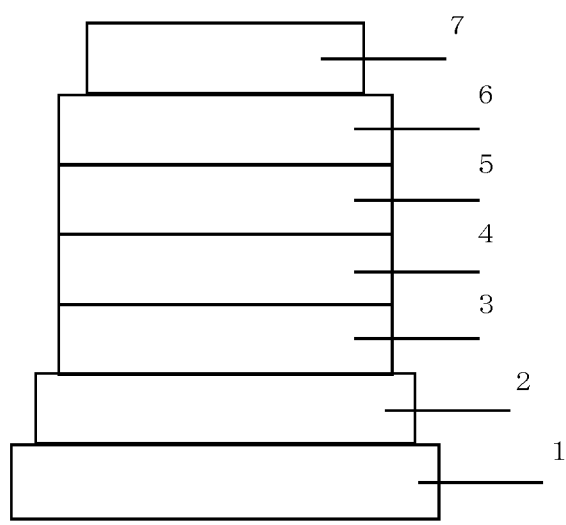

ORGANIC ELECTROLUMINESCENT DEVICE HAVING TRIPTYCENE DERIVATIVE MATERIAL

TECHNICAL FIELD

This invention relates to an organic electroluminescent device comprising a triptycene derivative and, more particularly, to a thin film type device which emits light upon application of an electrical field to a light-emitting layer composed of an organic compound.

An organic electroluminescent device (hereinafter referred to as organic EL device) in the simplest structure is generally constituted of a light-emitting layer and a pair of counter electrodes sandwiching the said light-emitting layer. The device functions by utilizing the following phenomenon; upon application of an electrical field between the electrodes, electrons are injected from the cathode and holes are injected from the anode and they recombine in the light-emitting layer with emission of light.

In recent years, organic thin films have been used in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (hereinafter referred to as Alq3) are disposed in thin film between the electrode. This device has brought about a marked improvement in the luminous efficiency over the conventional devices utilizing single crystals of anthracene and the like and thereafter the developmental works of organic EL devices have been directed toward commercial applications to high-performance flat panels featuring self-luminescence and high-speed response.

In another effort to enhance the luminous efficiency of the device, the use of phosphorescence in place of fluorescence is investigated. The aforementioned device comprising a hole-transporting layer composed of an aromatic diamine and a light-emitting layer composed of Alq3 and many other devices utilize fluorescence. The use of phosphorescence, that is, emission of light from the excited triplet state, is expected to enhance the luminous efficiency three to four times that of the conventional devices utilizing fluorescence (emission of light from the excited singlet state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they failed to emit light at high efficiency. In recent years, as stated in patent document 1, a large number of researches are conducted with the objective of enhancing the luminous efficiency and extending the lifetime while giving priority to utilization of organic metal complexes such as iridium complexes.

Patent document 1: JP2003-515897 A
Patent document 2: JP2001-313178 A
Patent document 3: JP2001-520255 A
Patent document 4: JP2002-015871 A
Patent document 5: JP2007-520875 A
Non-patent document 1: Applied Physics Letters, 2003, 83, 569-571
Non-patent document 2: Applied Physics Letters, 2003, 82, 2422-2424

In order to enhance the luminous efficiency, a host material to be used together with the aforementioned dopant material becomes important. Of the host materials proposed thus far, a typical example is 4,4'-bis(9-carbazolyl)biphenyl (hereinafter referred to as CBP), a carbazole compound cited in patent document 2. When used as a host material for tris(2-phenylpyridine)iridium complex (hereinafter referred to as Ir(ppy)3), a typical phosphorescent green light-emitting material, CBP displays relatively good luminous characteristics. On the other hand, when used as a host material for phosphorescent blue light-emitting materials, CBP fails to perform at sufficiently high luminous efficiency. This occurs for the following reason; the energy level of the lowest triplet excited state of CBP is lower than that of ordinary phosphorescent blue light-emitting materials and the triplet excitation energy of a phosphorescent blue light-emitting material is transferred to CBP. That is to say, if a phosphorescent host material were designed to have triplet excitation energy higher than that of a phosphorescent light-emitting material, the triplet excitation energy of the phosphorescent light-emitting material would be confined effectively and, as a result, the luminous efficiency would be enhanced. As described in non-patent document 1, the structure of CBP was modified to increase the triplet excitation energy for the purpose of improving this energy-confining effect and the host material thus modified enhanced the luminous efficiency of bis[2-(4,6-difluorophenyl)pyridinato-N,C2']iridium picolinate (hereinafter referred to as Flrpic). Further, as described in non-patent document 2, the luminous efficiency was enhanced similarly by using 1,3-dicarbazolylbenzene (hereinafter referred to as mCP) as a host material. However, these materials were not satisfactory for practical use, particularly from the viewpoint of durability.

Moreover, in order to enhance the luminous efficiency, a host material needs to have a good balance of injection/transport properties of electrical charges (holes and electrons). The electron transport ability is inferior to the hole transport ability in the case of CBP and this destroys the balance of electrical charges in the light-emitting layer and causes excess holes to flow out to the side of the cathode thereby reducing the probability of recombination of holes and electrons in the light-emitting layer and eventually lowering the luminous efficiency. Furthermore, in this case, the recombination zone in the light-emitting layer is limited to a narrow region in the vicinity of the interface on the cathode side; consequently, when an electron-transporting material like Alq3 whose energy level of the lowest triplet excited state is lower than that of Ir(ppy)3 is used, there may arise the possibility that the luminous efficiency becomes lower due to transfer of the triplet excitation energy from the dopant to the electron-transporting material.

As stated above, in order to enhance the luminous efficiency of an organic EL device, a host material which has high triplet excitation energy and is balanced well in the injection/transport properties of electrical charges (holes and electrons) is needed. Furthermore, it is desirable that such a host material shows electrochemical stability, high heat resistance, and excellent stability in the amorphous state. However, no compound which satisfies these properties on a practical level is known yet at the present.

In patent document 3, a triptycene derivative illustrated below and others are cited as examples of light-emitting materials.

In patent document 4, a triptycene derivative illustrated below and others are cited as examples of light-emitting materials.

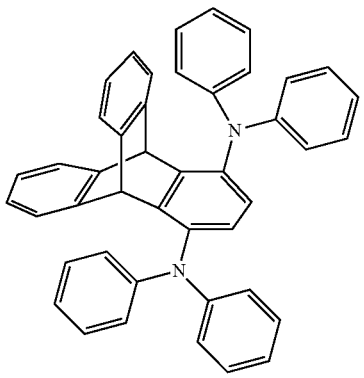 [SMILES: c1ccc(N(c2ccccc2)c2ccc(N(c3ccccc3)c3ccccc3)c3c2C2c4ccccc4C3c3ccccc32)cc1]

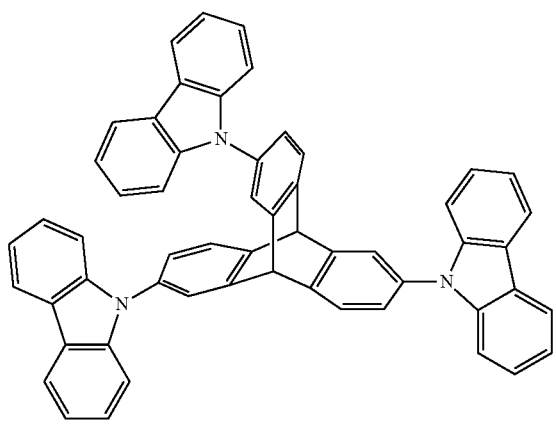 [SMILES: c1ccc2c(c1)c1ccccc1n2-c1ccc2c(c1)C1c3ccc(-n4c5ccccc5c5ccccc54)cc3C2c2cc(-n3c4ccccc4c4ccccc43)ccc21]

However, the compounds disclosed concretely in patent documents 3 and 4 contain two active benzylic protons and, as a result, they show poor stability and organic EL devices in which they are incorporated display extremely poor durability.

Further, in patent document 5, a triptycene derivative illustrated below is cited as a material for the hole-blocking layer.

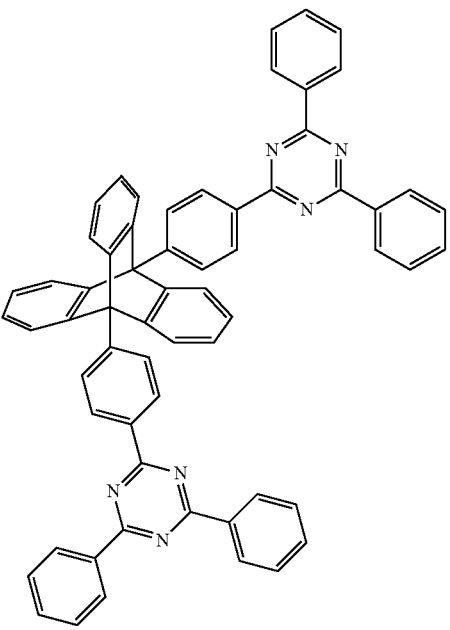 [SMILES: c1ccc(-c2nc(-c3ccccc3)nc(-c3ccc(C45c6ccccc6C(c6ccc(-c7nc(-c8ccccc8)nc(-c8ccccc8)n7)cc6)(c6ccccc64)c4ccccc45)cc3)n2)cc1]

In patent document 5, a heterocycle which has a good electron transport property (such as triazine) is considered essential and a triptycene skeleton which has an electron transport property is disclosed as a basic skeleton for such a heterocycle. The document discloses no more than the function of the triptycene derivative as a material for the hole-blocking layer and does not teach compounds substituted with a diarylamine-derived group which has a hole transport property or usefulness of the trypticene derivative as a hole-transporting material for the hole-transporting layer or as a host material for the light-emitting layer.

SUMMARY OF THE INVENTION

In applications of organic EL devices to display devices such as flat panel displays, it is necessary to improve the luminous efficiency of the device and, at the same time, to fully secure the driving stability of the device. Under the aforementioned circumstances, an object of this invention is to provide an organic EL device endowed with such high luminous efficiency and driving stability as to be practically useful and to provide a compound suitable therefor.

The inventors of this invention have conducted intensive studies and found that endcapping benzylic protons of triptycene which markedly degrade the durability of an organic EL device with aromatic groups can improve the durability. They have further found that bonding of a diarylamine-derived group which has a good hole transport property produces a good balance of electrical charges due to the electron transport property of triptycene and the hole transport property of a diarylamine. This invention has been completed on the basis of the finding that organic EL devices in which a group of compounds having the aforementioned properties is incorporated display excellent characteristics.

This invention relates to an organic electroluminescent device constituted of an anode, organic layers containing a phosphorescent light-emitting layer, and a cathode piled one upon another on a substrate wherein a triptycene derivative represented by the following general formula (1) is contained in at least one organic layer selected from the group of a phosphorescent light-emitting layer, a hole-transporting layer, an electron-blocking layer, and an exciton-blocking layer.

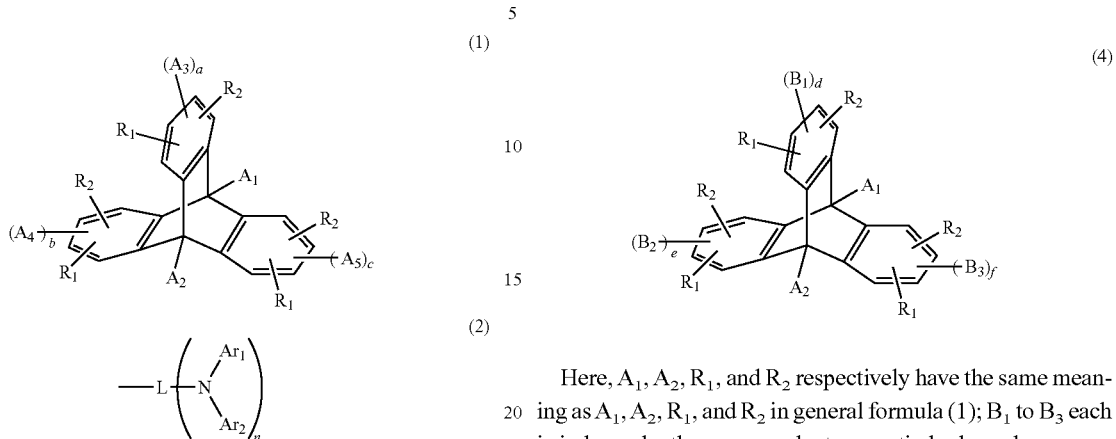

(1)

(2)

In general formula (1), $A_1$ to $A_5$ each is independently a group represented by formula (2); a, b, and c each is an integer of 0-2 and $0 \leq a+b+c \leq 3$; $R_1$ and $R_2$ each is independently hydrogen, an alkyl group of 1-10 carbon atoms, an alkoxyl group of 1-6 carbon atoms, or an acyl group of 2-6 carbon atoms.

In formula (2), n is an integer of 0-2 and the sum of n's is 1-5; L is a direct bond, an (n+1)-valent aromatic hydrocarbon group of 6-18 carbon atoms, or an (n+1)-valent aromatic heterocyclic group of 3-17 carbon atoms or, when n is 0, L is a monovalent aromatic hydrocarbon group of 6-18 carbon atoms or a monovalent aromatic heterocyclic group of 3-17 carbon atoms; $Ar_1$ and $Ar_2$ each is independently an aromatic hydrocarbon group of 6-18 carbon atoms or an aromatic heterocyclic group of 3-17 carbon atoms and $Ar_1$, $Ar_2$, and the nitrogen together may form a nitrogen-containing heterocycle.

In general formula (1), it is preferable that $A_1$ to $A_5$ each is independently represented by formula (3).

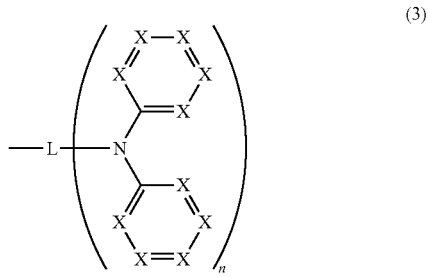

(3)

Here, L and n respectively have the same meaning as L and n in formula (2); X is independently a methine group or nitrogen; the two aromatic rings and the nitrogen atom to which they are bonded may be fused to form a three-membered ring with a ring containing the said nitrogen atom located at the center.

Of the triptycene derivatives represented by general formula (1), those which are represented by the following general formula (4) are preferred.

(4)

Here, $A_1$, $A_2$, $R_1$, and $R_2$ respectively have the same meaning as $A_1$, $A_2$, $R_1$, and $R_2$ in general formula (1); $B_1$ to $B_3$ each is independently a monovalent aromatic hydrocarbon group of 6-18 carbon atoms or a monovalent aromatic heterocyclic group of 3-17 carbon atoms; d, e, and f each is an integer of 0-2 and $0 \leq d+e+f \leq 3$.

This invention further relates to an organic electroluminescent device wherein an organic layer containing the aforementioned triptycene derivative is a light-emitting layer containing a phosphorescent dopant.

BRIEF DESCRIPTION OF THE DRAWING

FIG. 1 schematically illustrates the cross section of an example of an organic EL device.

PREFERRED EMBODIMENTS OF THE INVENTION

An organic electroluminescent device according to this invention contains a triptycene derivative represented by the aforementioned general formula (1).

In general formula (1), $A_1$ to $A_5$ each is independently a group represented by the aforementioned general formula (2); a, b, and c each is independently an integer of 0-2 and a+b+c is an integer of 0-3, preferably 0 or 1.

The groups $R_1$ and $R_2$ each is independently hydrogen, an alkyl group of 1-10 carbon atoms, an alkoxyl group of 1-6 carbon atoms, or an acyl group of 2-6 carbon atoms: preferably, hydrogen, an alkyl group of 1-4 carbon atoms, an alkoxyl group of 1-4 carbon atoms, or an acyl group of 2-4 carbon atoms; more preferably, hydrogen, an alkyl group of 1-2 carbon atoms, an alkoxyl group of 1-2 carbon atoms, or an acetyl group; most preferably, hydrogen.

In general formula (2), n is an integer of 0-2 and the sum of n's is 1-5; that is to say, the sum of the aforementioned integers designated as n in general formula (1) is 1-5. It is to be understood that the number of groups represented by formula (2) contained in a triptycene derivative represented by general formula (1) is 2+(a+b+c) or 2-5 and, since n in formula (2) is an integer of 0, 1, or 2, the sum of the integers which [2+(a+b+c)]n's can take is 1-5.

The group L is a direct bond, an (n+1)-valent aromatic hydrocarbon group of 6-18 carbon atoms, or an (n+1)-valent aromatic heterocyclic group of 3-17 carbon atoms or, when n is 0, L is a monovalent aromatic hydrocarbon group of 6-18 carbon atoms or a monovalent aromatic heterocyclic group of 3-17 carbon atoms. That is, n ring carbon atoms of the aromatic hydrocarbon group or aromatic heterocyclic group are bonded to —NAr$_1$Ar$_2$ groups while one ring carbon atom of the said group is bonded to a ring carbon atom of triptycene and, when n is 0, one ring carbon atom of the said group is bonded to a ring carbon atom of triptycene. As stated above, not all of n's are 0 and the sum of n's is 1-5 and this means that the number of —NAr$_1$Ar$_2$ groups in a triptycene derivative represented by general formula (1) is 1-5, preferably 1-3.

Examples of the aforementioned aromatic hydrocarbon groups and aromatic heterocyclic groups include the groups derived from benzene, pyridine, pyrimidine, triazine, biphenyl, naphthalene, quinoline, isoquinoline, quinoxaline, and naphthyridine, preferably from benzene, pyridine, and pyrimidine. Furthermore, the aromatic hydrocarbon groups and aromatic heterocyclic groups may have substituents to be described later.

The groups Ar$_1$ and Ar$_2$ each is independently an aromatic hydrocarbon group of 6-18 carbon atoms or an aromatic heterocyclic group of 3-17 carbon atoms and Ar$_1$, Ar$_2$, and the nitrogen atom together may form a nitrogen-containing heterocycle. Preferable examples of Ar$_1$ and Ar$_1$ include the monovalent groups derived from benzene, pyridine, pyrimidine, triazine, biphenyl, naphthalene, quinoline, isoquinoline, quinoxaline, and naphthyridine. A phenyl group is preferred.

In the case where Ar$_1$, Ar$_2$, and the nitrogen atom together form a nitrogen-containing heterocycle, the said nitrogen-containing heterocycle is preferably a five- or six-membered ring; other rings may be further fused to the said heterocycle to form a fused ring preferably having a structure obtained by fusing two other rings to the nitrogen-containing heterocycle at the center. Preferable examples of such nitrogen-containing heterocycles include carbazole, acridine, and benzocarbazole.

In the case where the aforementioned L, Ar$_1$, or Ar$_2$ is an aromatic hydrocarbon group or an aromatic heterocyclic group, the aromatic hydrocarbon group or the aromatic heterocyclic group may have substituents. Likewise, in the case where Ar$_1$, Ar$_2$, and the nitrogen atom together form a nitrogen-containing heterocycle, the nitrogen-containing heterocycle may have substituents. Examples of such substituents include an alkyl group of 1-4 carbon atoms, an alkoxyl group of 1-2 carbon atoms, an acetyl group, and an aryl group of 6-18 carbon atoms; preferably a methyl group, a methoxy group, an acetyl group, and a phenyl group; more preferably a methyl group or a phenyl group. Advantageously, the aforementioned aromatic hydrocarbon group, aromatic heterocyclic group, or nitrogen-containing heterocycle is free of substituents or has one or two methyl or phenyl groups. In the case where the aromatic hydrocarbon group, aromatic heterocyclic group, or nitrogen-containing heterocycle has substituents, the number of carbon atoms in the group is calculated by including the number of carbon atoms in the substituents.

Although A$_1$ to A$_5$ each is independently represented by formula (2) in general formula (1), a group represented by the aforementioned formula (3) is preferable to a group represented by formula (2).

In formula (3), L and n respectively have the same meaning as L and n in formula (2). Preferably, n is 1 or 2. The group X is independently a methine group or nitrogen, preferably a methine group. The two aromatic rings which are bonded to the nitrogen atom may be fused together to form a three-membered ring with a ring containing the said nitrogen atom located at the center. Preferably, the three-membered ring is a carbazole ring. The aforementioned methine group or the three-membered ring may have substituents. Preferable examples of such substitutents are the same as those described earlier for Ar$_1$ and Ar$_2$.

Of the triptycene derivatives represented by general formula (1), those which are represented by the aforementioned general formula (4) are preferred.

In general formula (4), A$_1$, A$_2$, R$_1$, and R$_2$ respectively have the same meaning as A$_1$, A$_2$, R$_1$, and R$_2$ in general formula (1). The groups B$_1$ to B$_3$ each is a substituent represented by formula (2) and n in formula (2) is 0 for each of them. Consequently, B$_1$ to B$_3$ each is independently a monovalent aromatic hydrocarbon group of 6-18 carbon atoms or an aromatic heterocyclic group of 3-17 carbon atoms. The symbols d, e, and f each is an integer of 0-2 and d+e+f=0-3. The integer n in formula (2) is 1 or 2 in at least one of A$_1$ and A$_2$ and the sum of n's in A$_1$ and A$_2$ is an integer of 1-4, preferably 1 or 2.

The groups B$_1$ to B$_3$ each has the same meaning as L when n is 0 and, as explained on that occasion, each denotes a monovalent aromatic hydrocarbon group of 6-18 carbon atoms or a monovalent aromatic heterocyclic group of 3-17 carbon atoms. Concretely, examples of B$_1$ to B$_3$ include the groups derived from benzene, pyridine, pyrimidine, triazine, biphenyl, naphthalene, quinoline, isoquinoline, quinoxaline, and naphthyridine, preferably from benzene and pyridine. The aforementioned aromatic hydrocarbon groups and aromatic heterocyclic groups may have substituents which are the same as those explained earlier.

Any of the triptycene derivatives represented by general formula (1) or (4) can be synthesized by a known method while selecting raw materials according to the structure of the target compound.

Several methods are available for the synthesis of the aforementioned triptycene derivatives: (1) benzyne prepared from anthranilic acid and isoamyl nitrite is reacted with a halogenated anthracene to give a halogenated triptycene and the halogenated triptycene is reacted with a variety of boronic acids in toluene in the presence of a palladium catalyst; (2) a halogenated anthracene is first reacted with a variety of boronic acids in toluene in the presence of a palladium catalyst and finally reacted with benzyne prepared from anthranilic acid and isoamyl nitrite.

Examples of the triptycene derivatives represented by general formula (1) are shown below, but are not limited thereto. The number assigned to the chemical formula is the compound number.

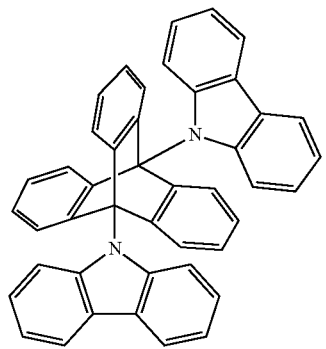
1
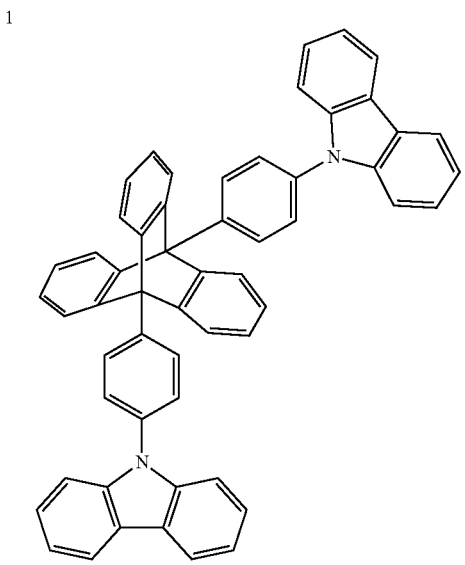
2
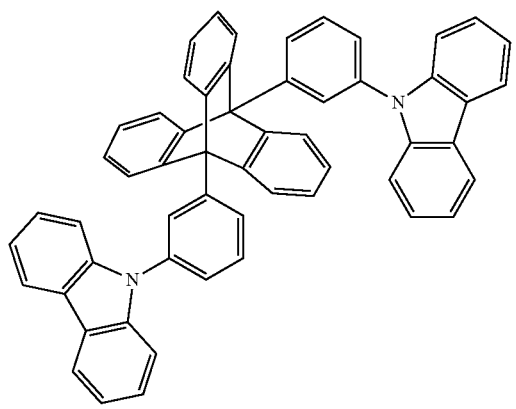
3
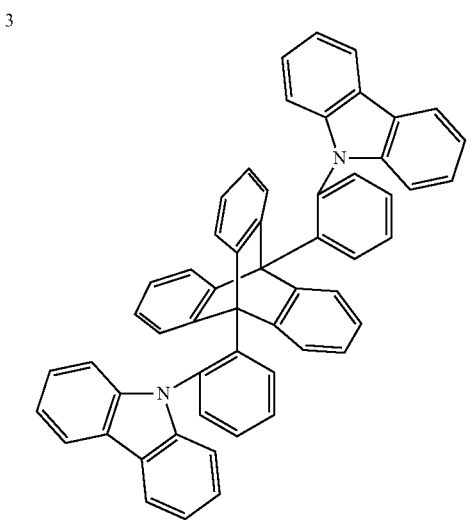
4
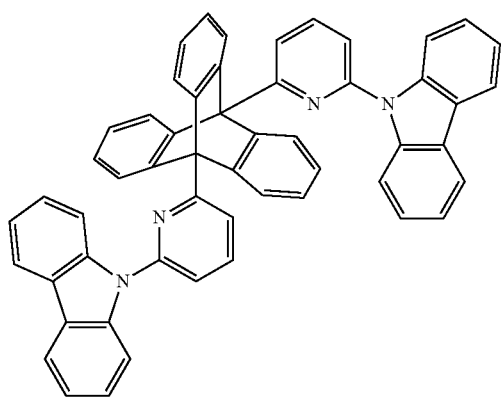
5
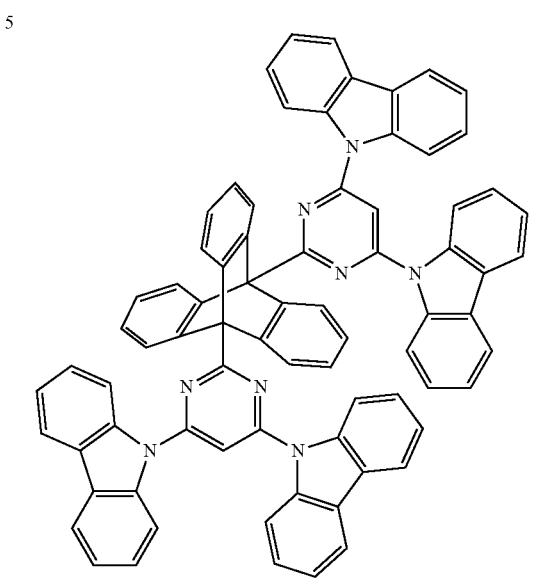
6

-continued
7
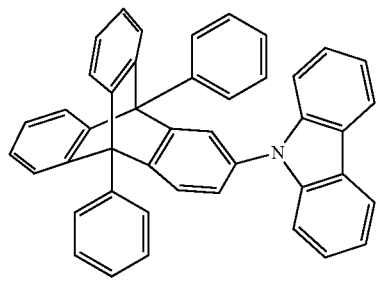
8
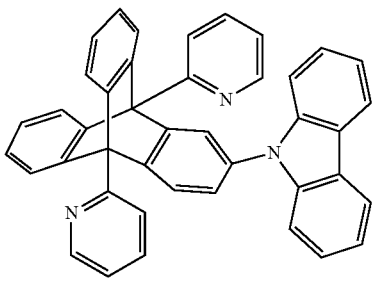
9
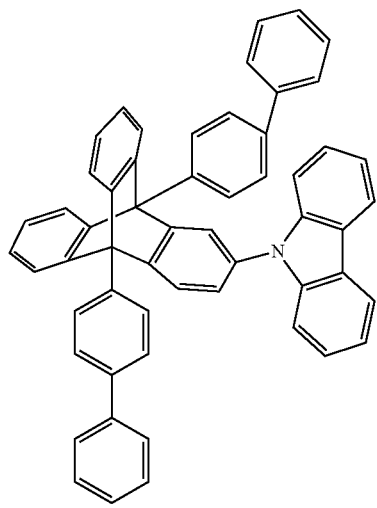
10
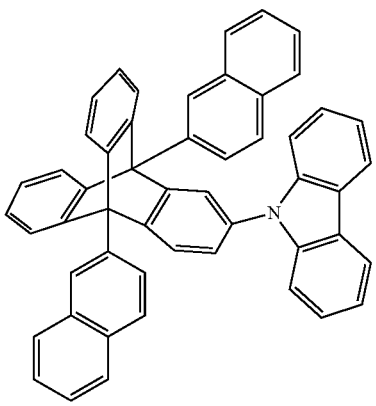
11
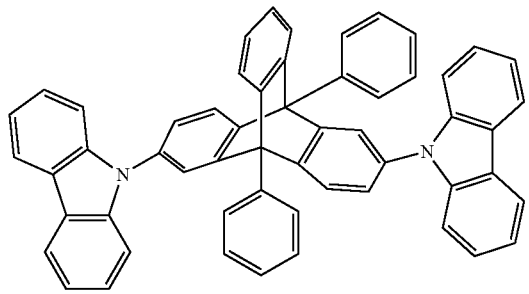
12
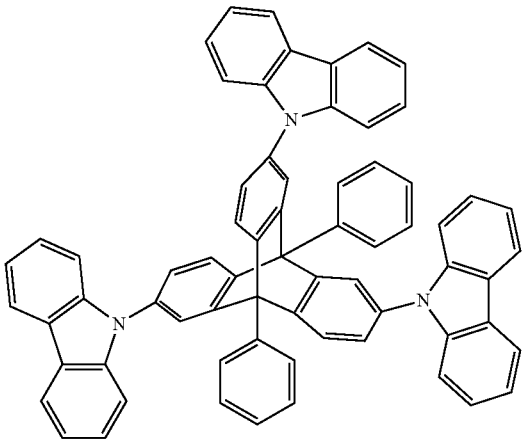

-continued
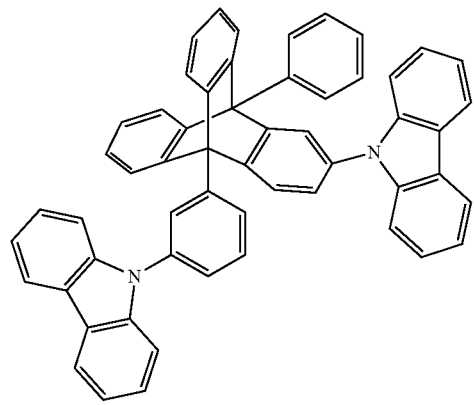
13
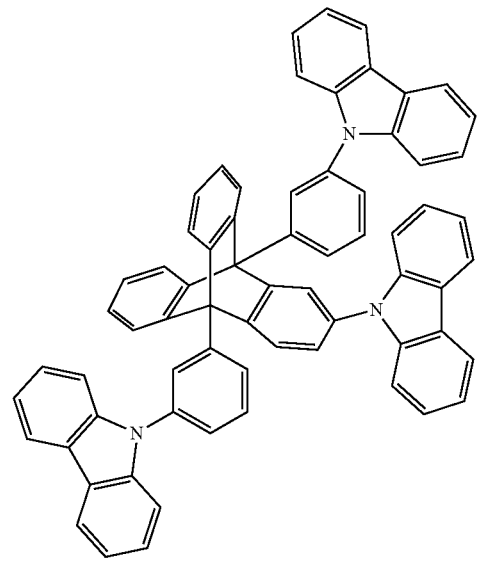
14
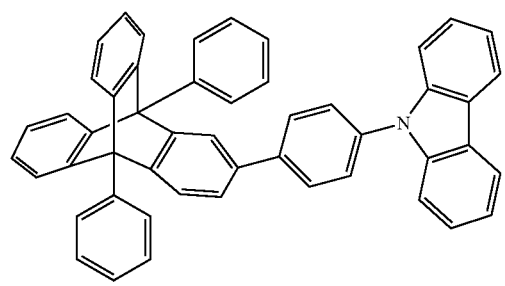
15
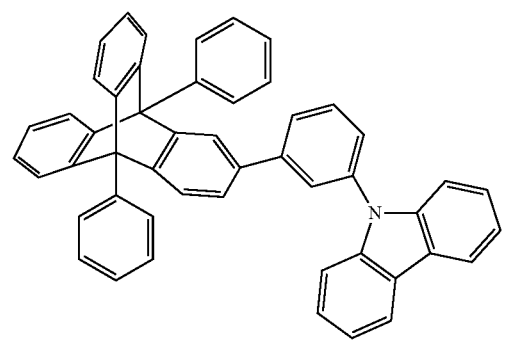
16
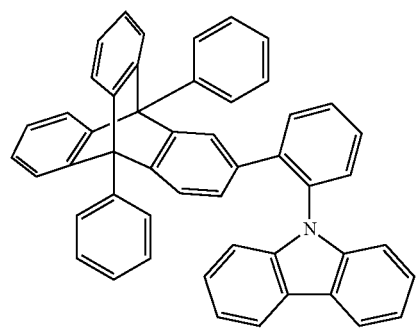
17
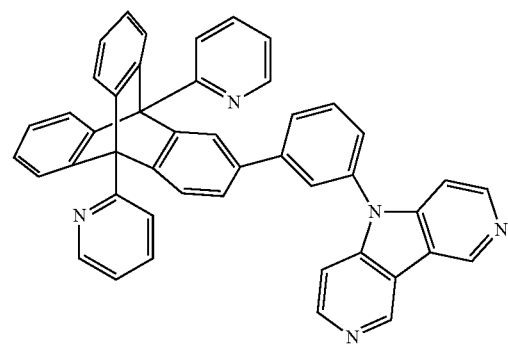
18

19
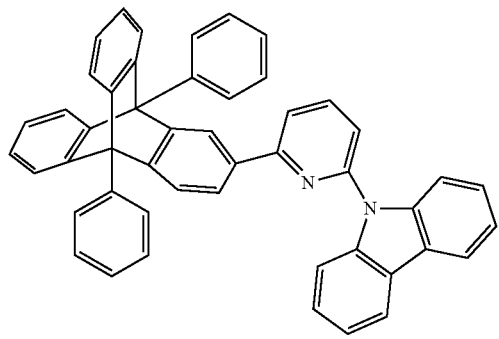
20
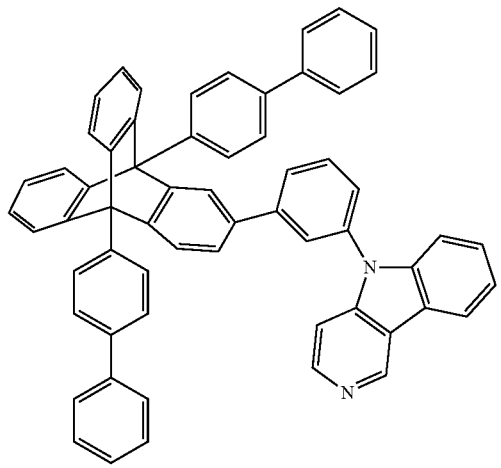
21
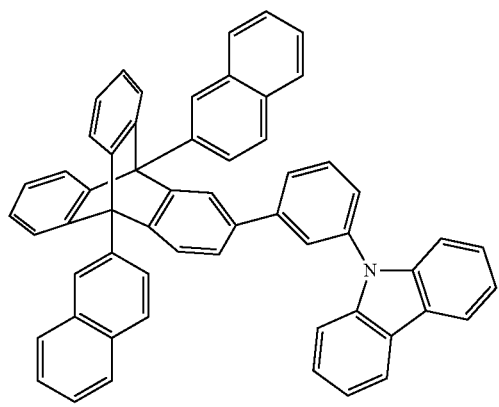
22
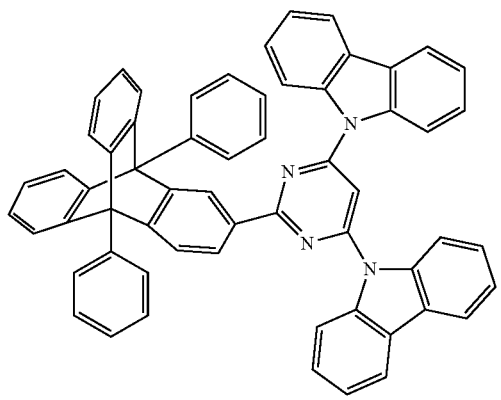
23
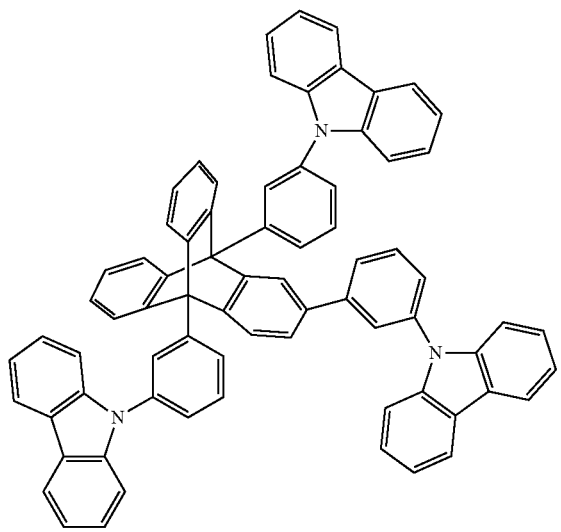
24
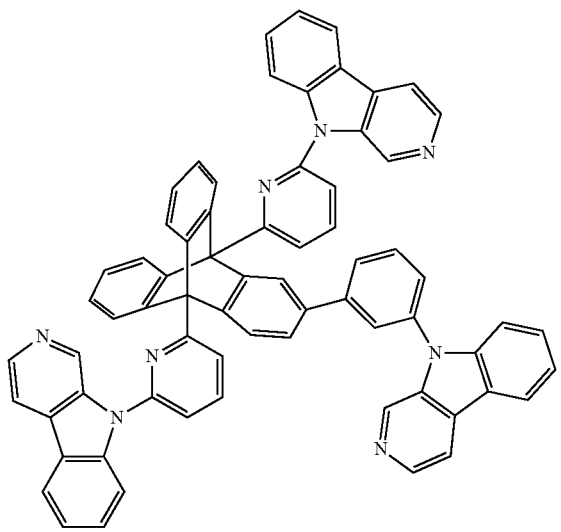

-continued
25
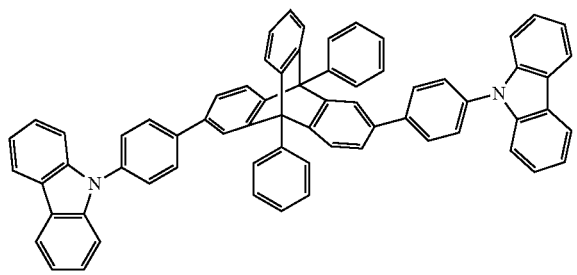
26
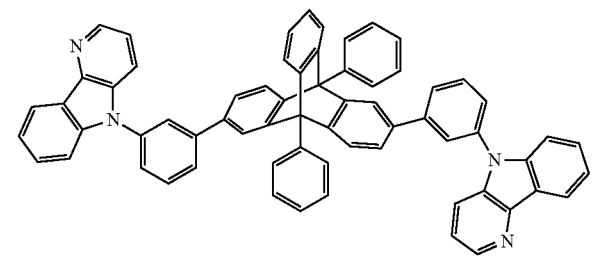
27
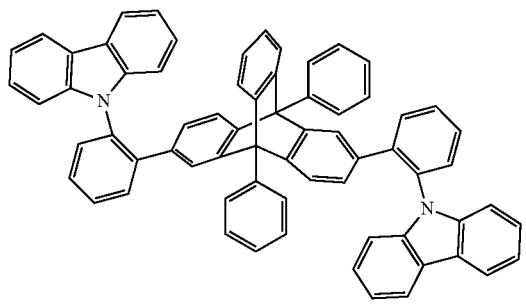
28
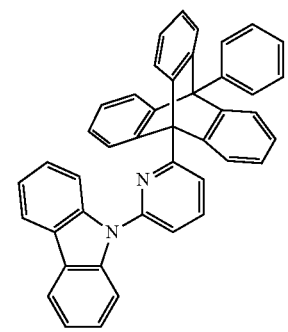
29
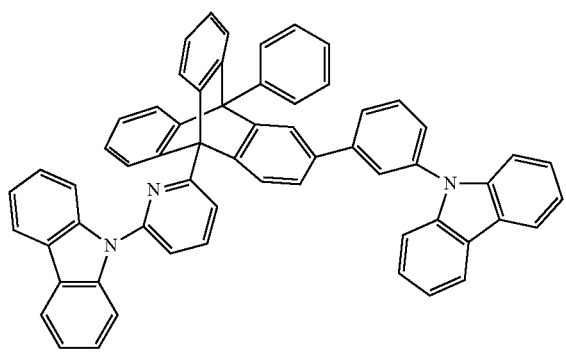
30
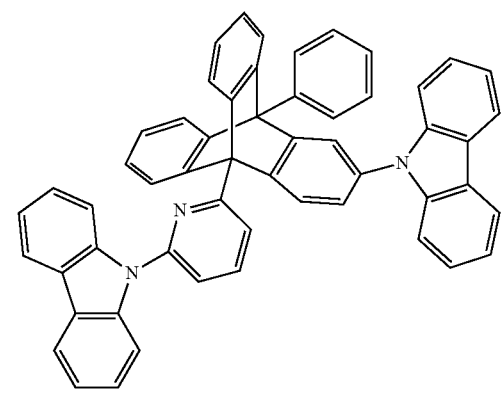
31
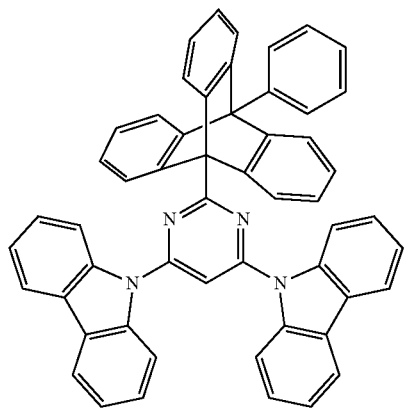
32
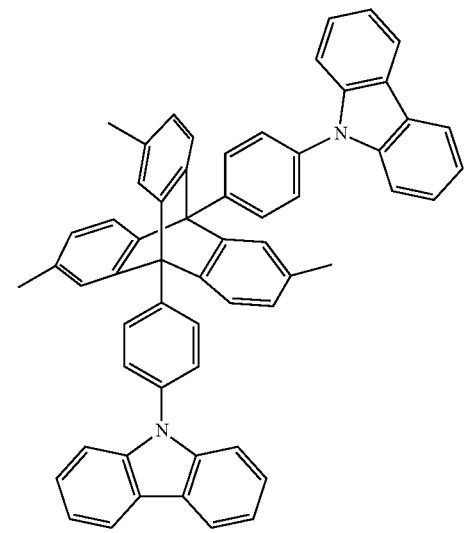

-continued
33
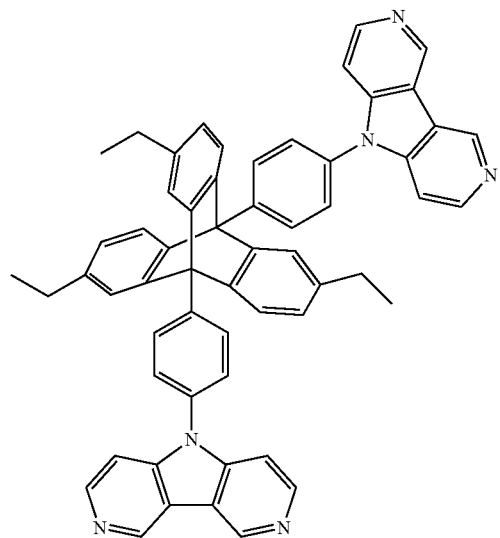
34
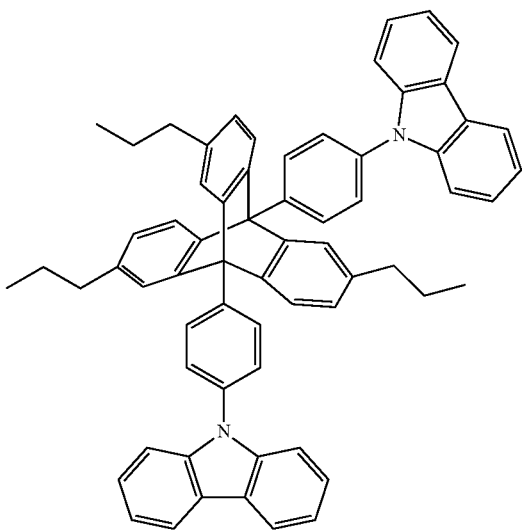
35
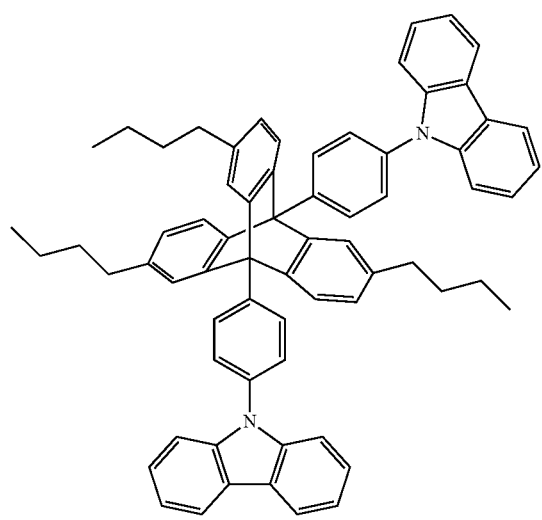
36
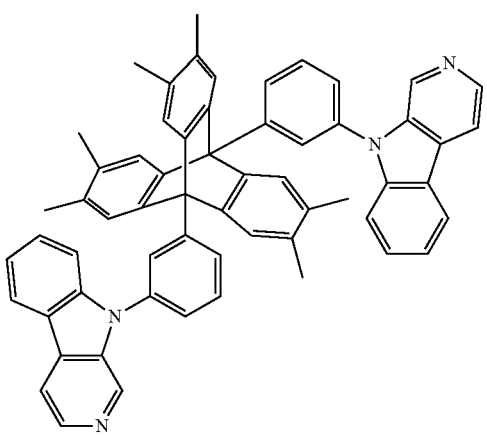
37
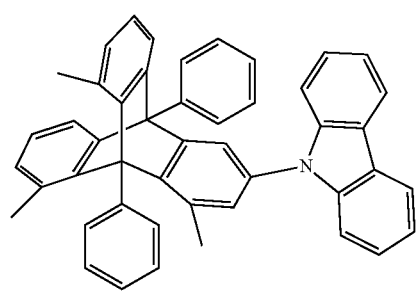
38
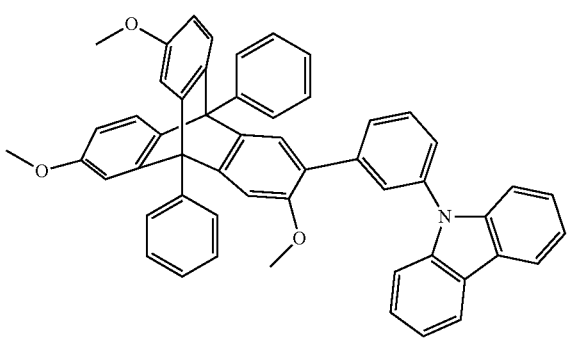

-continued
39
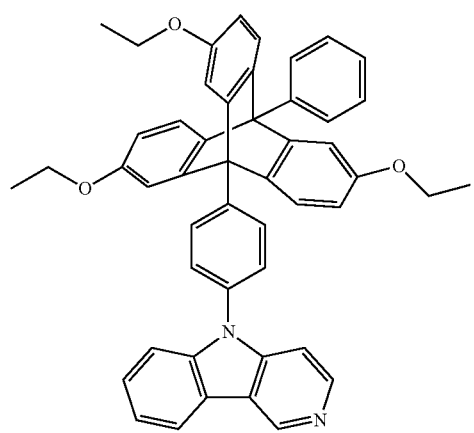
40
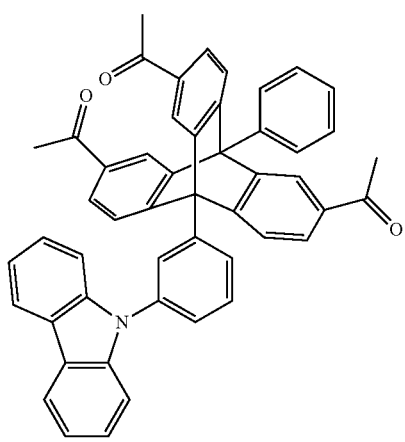
41
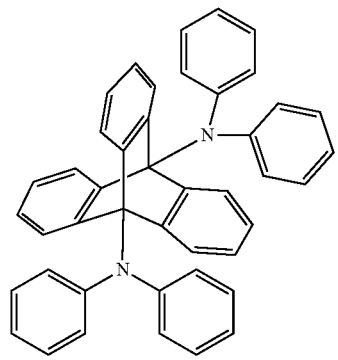
42
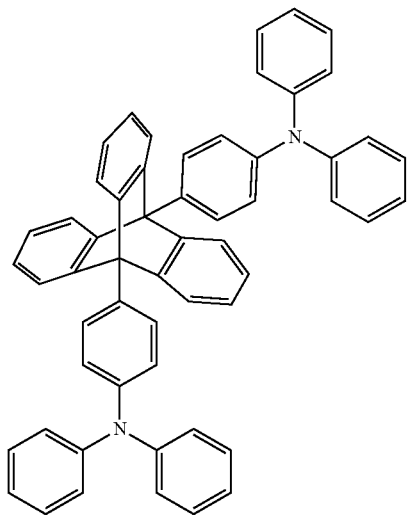
43
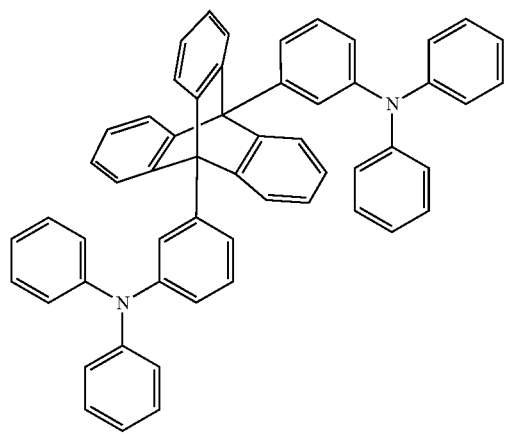
44
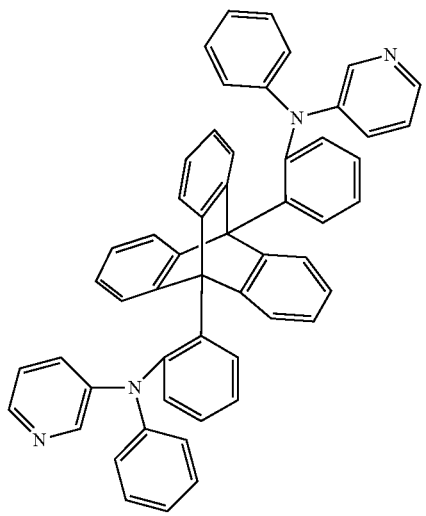

45
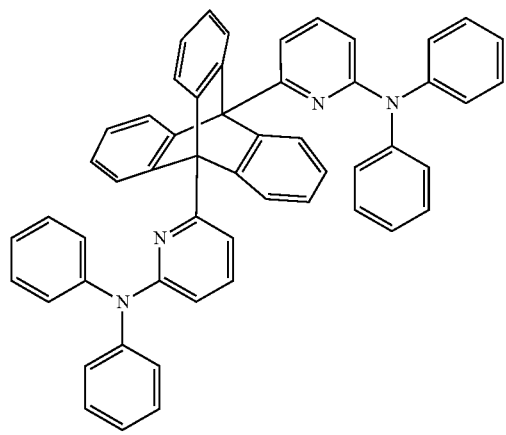
46
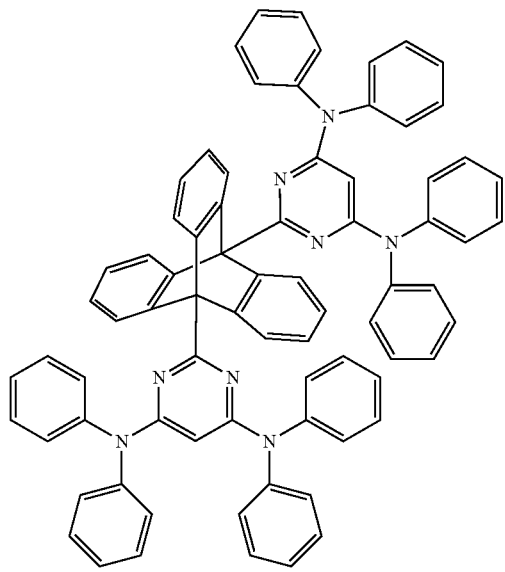
47
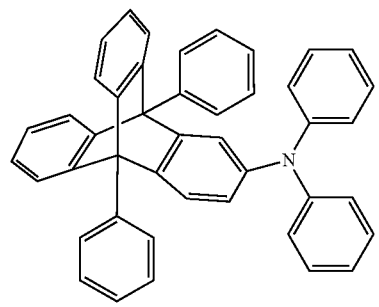
48
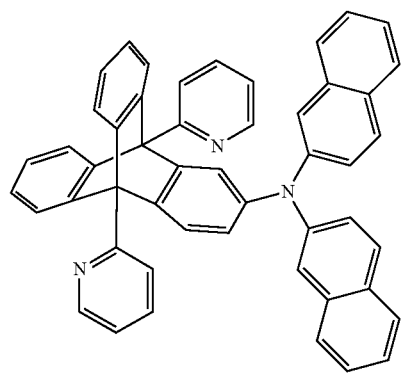
49
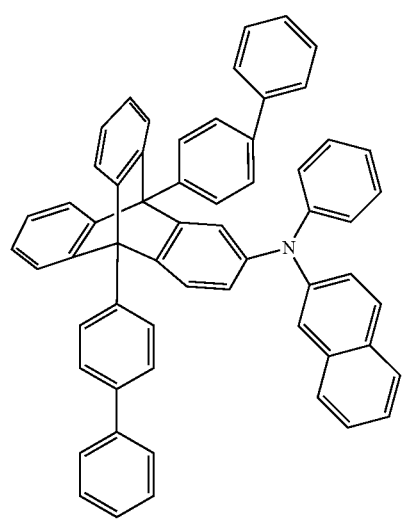
50
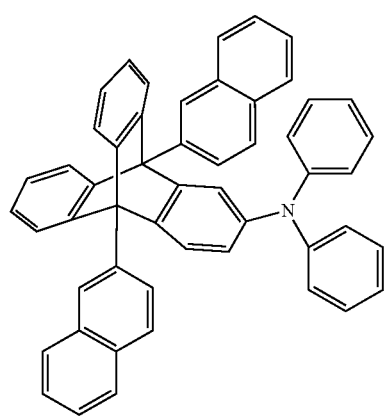

-continued
51
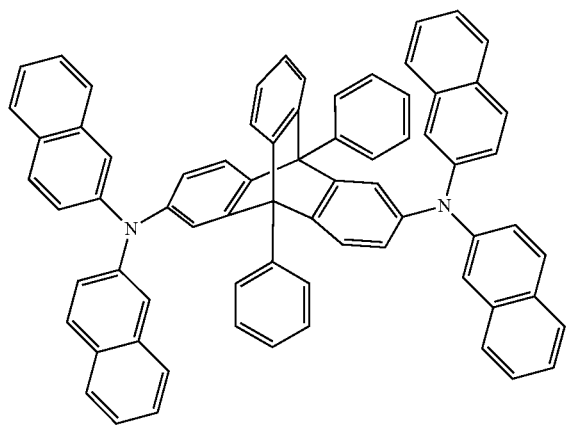
52
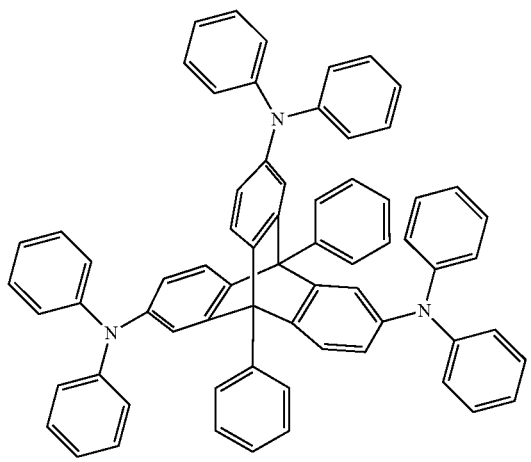
53
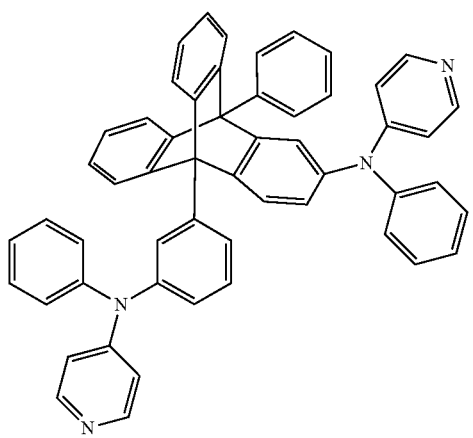
54
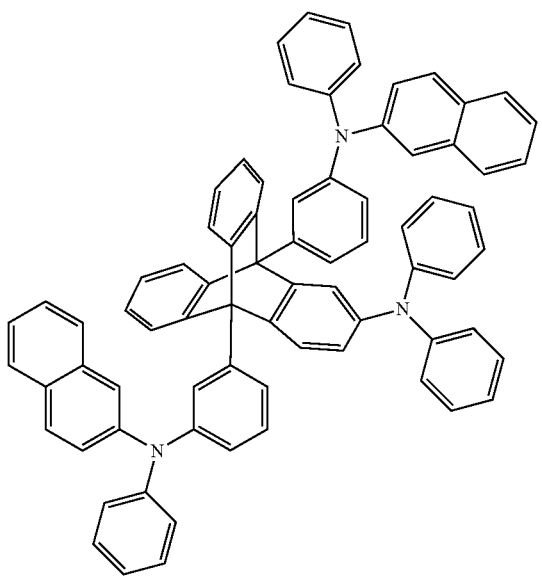
55
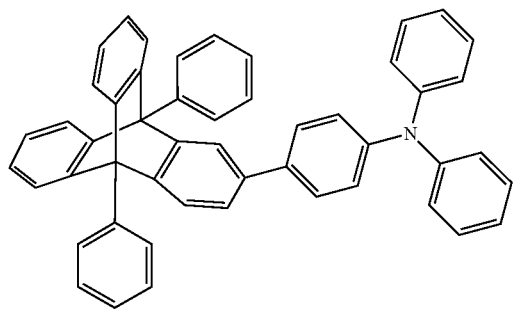
56
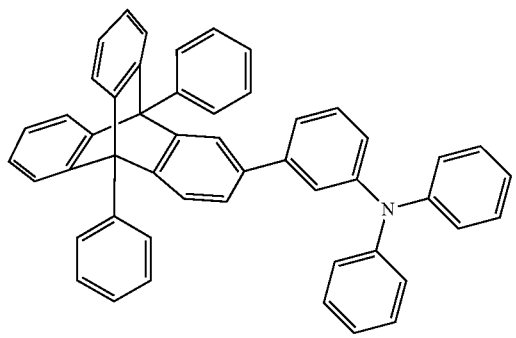

-continued
57
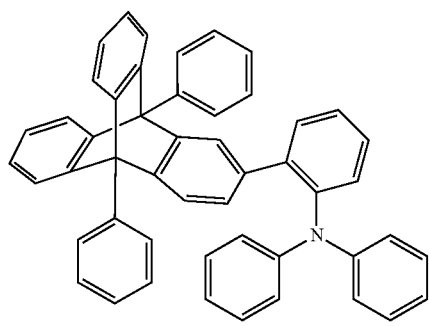
58
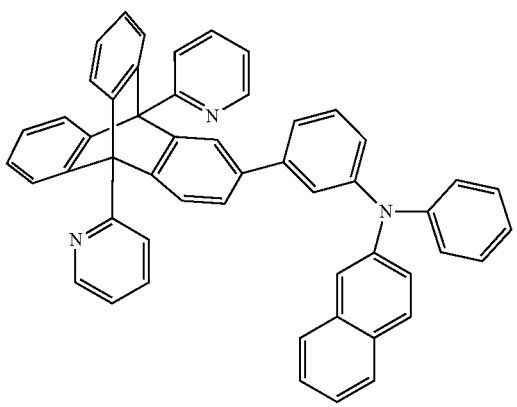
59
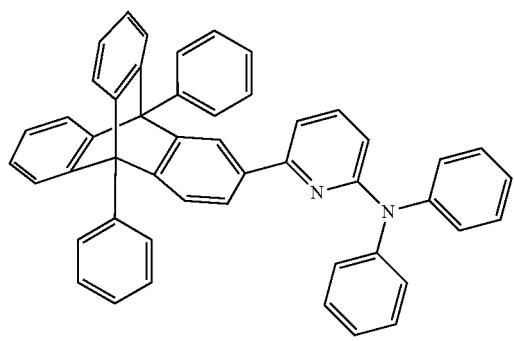
60
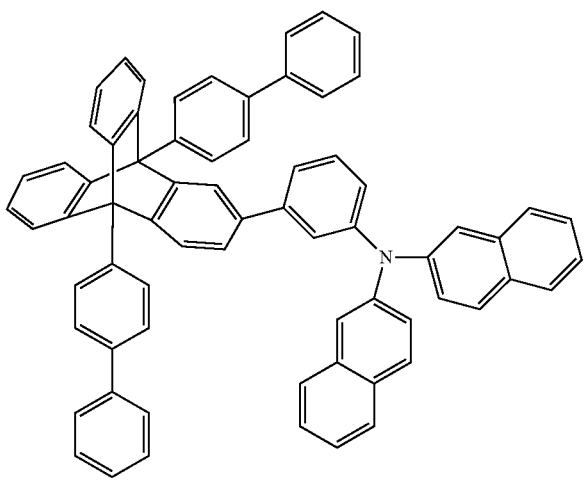
61
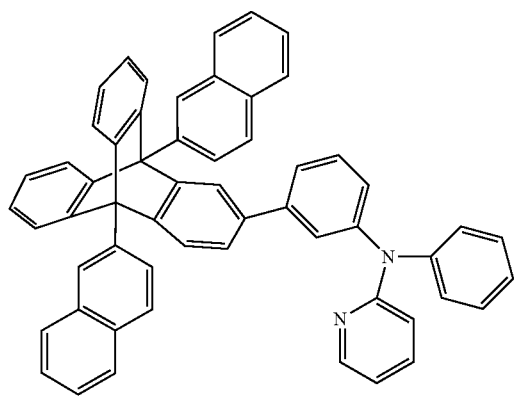
62
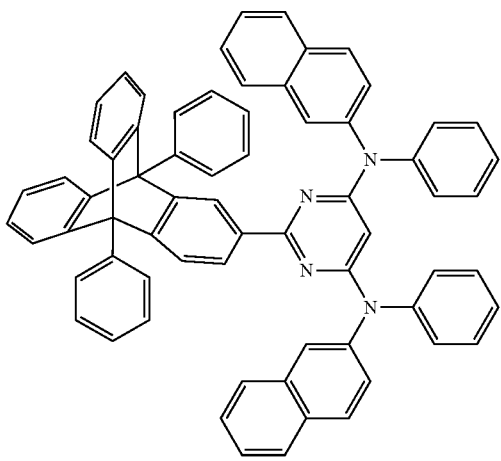

63
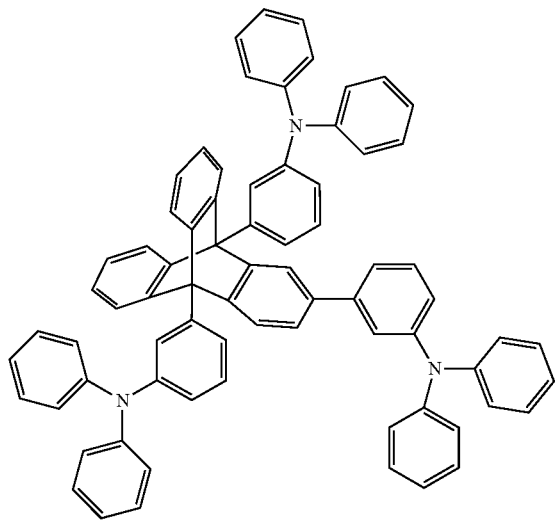
64
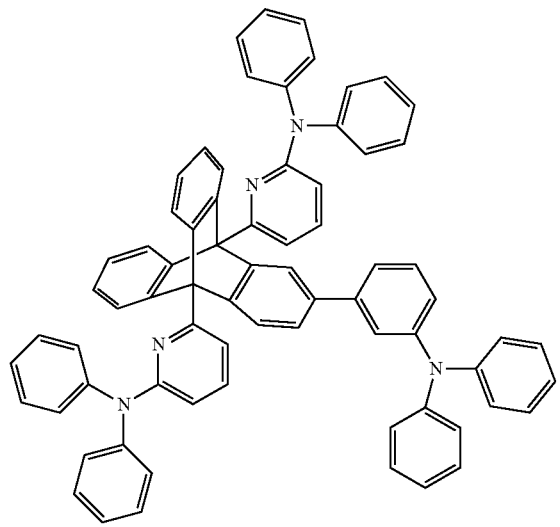
63
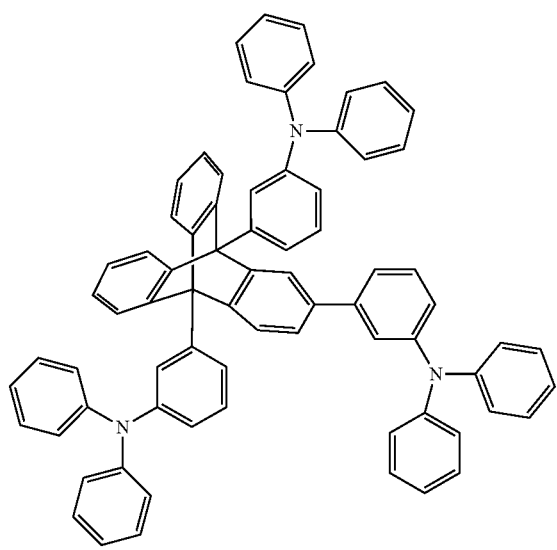
65
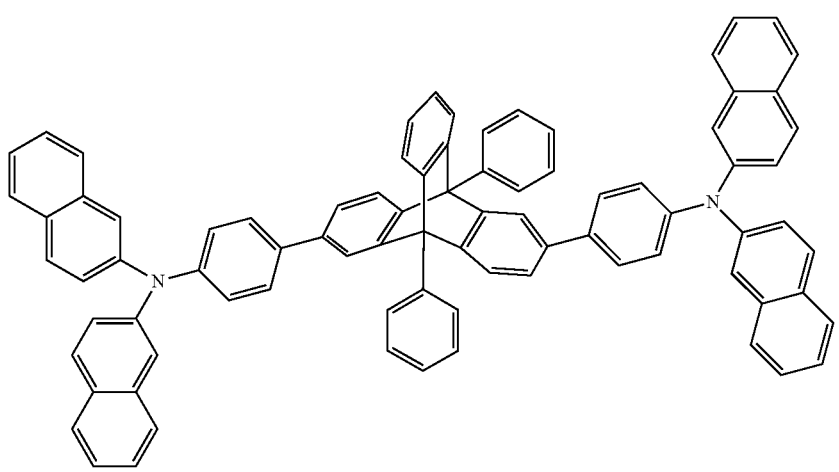

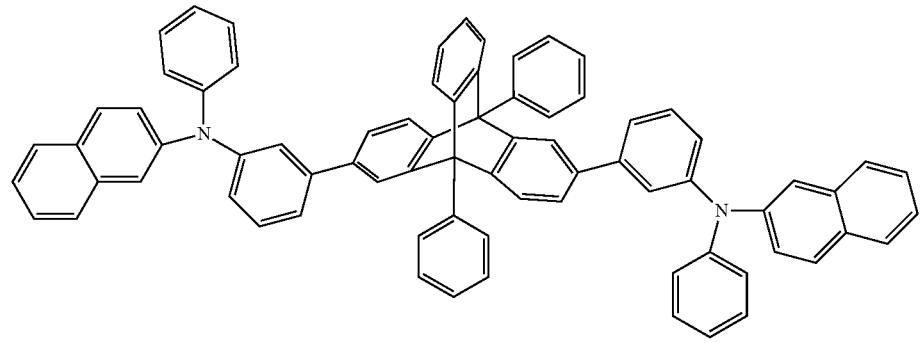
66
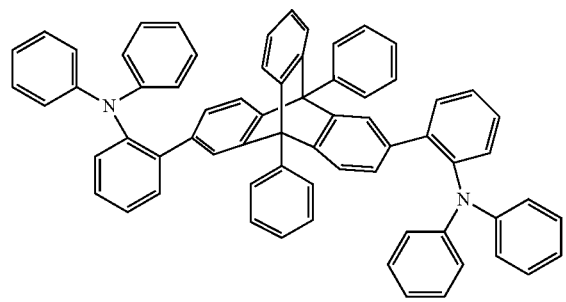
67
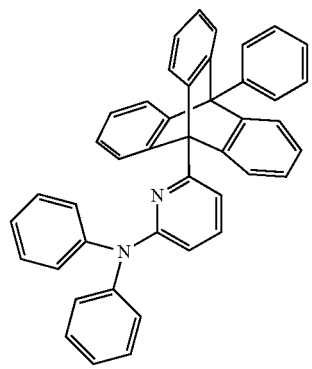
68
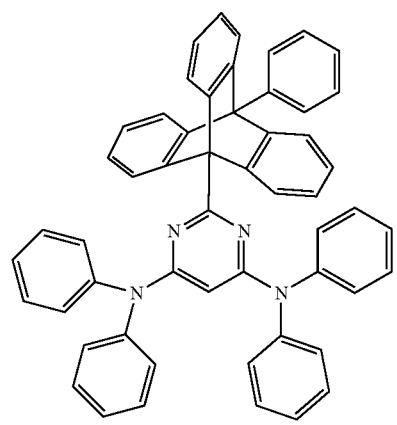
69
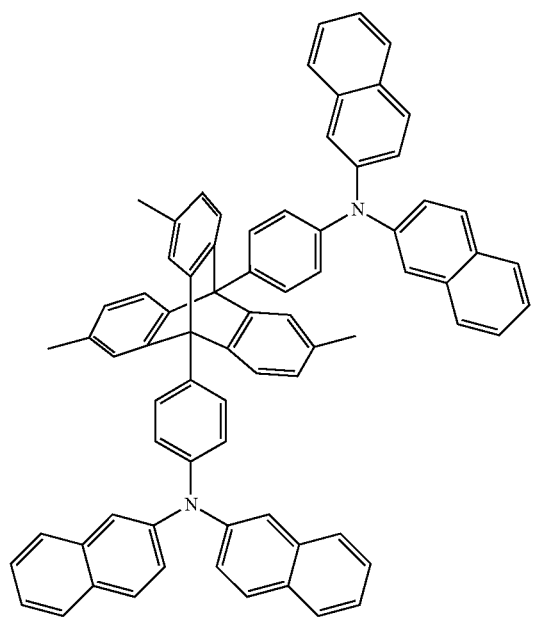
70

-continued
71
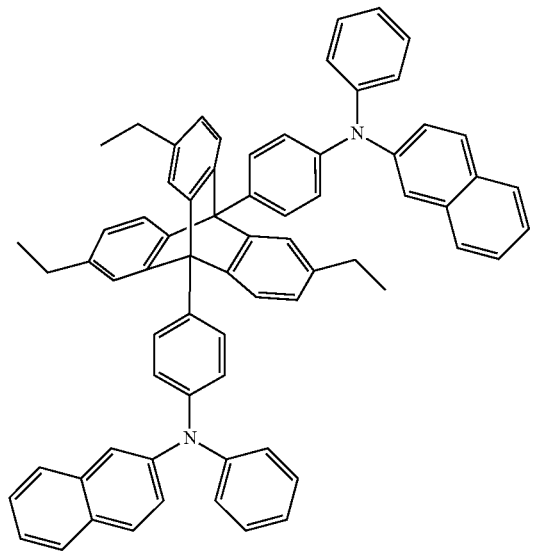
72
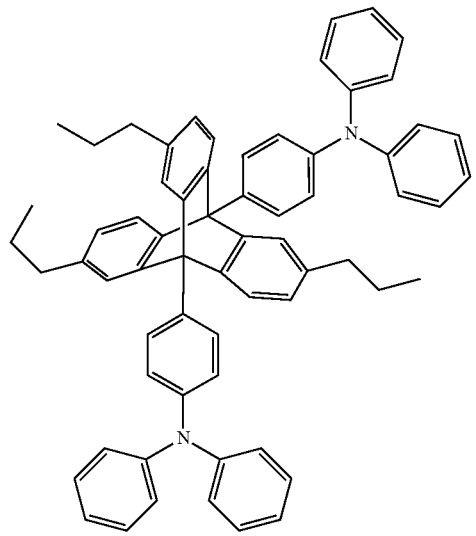
73
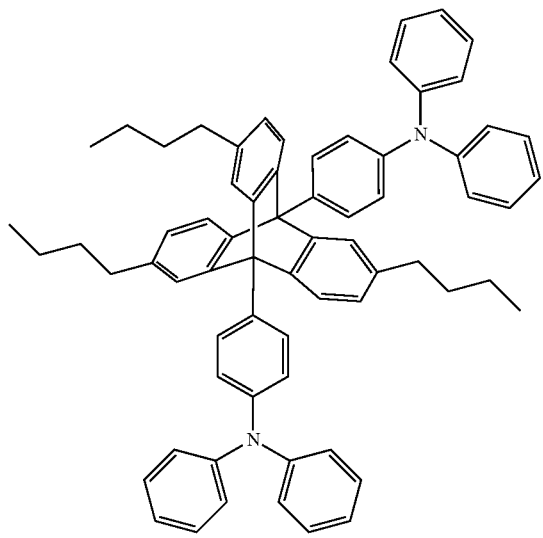
74
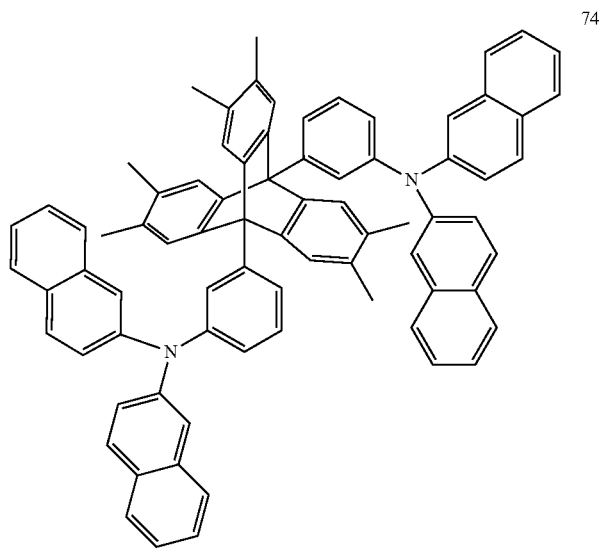
75
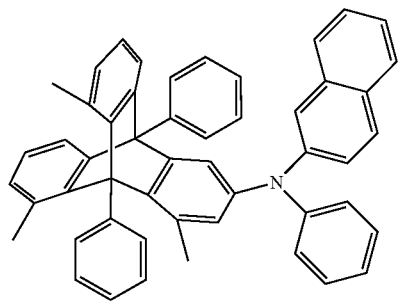
76
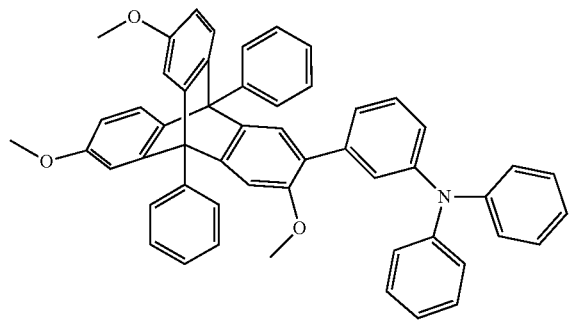

-continued
75
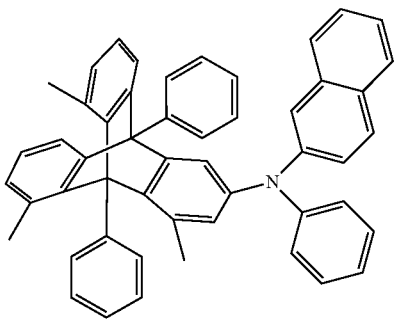
77
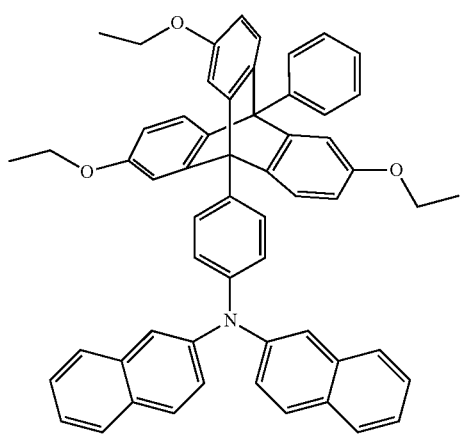
77
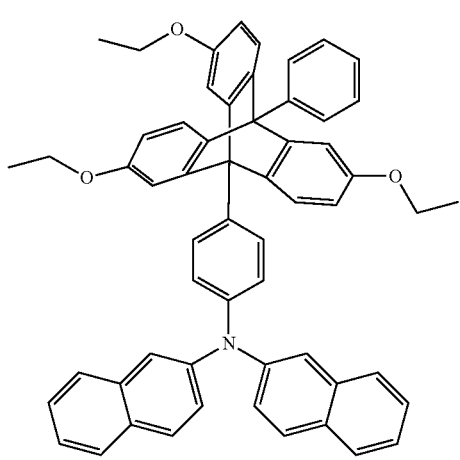
78
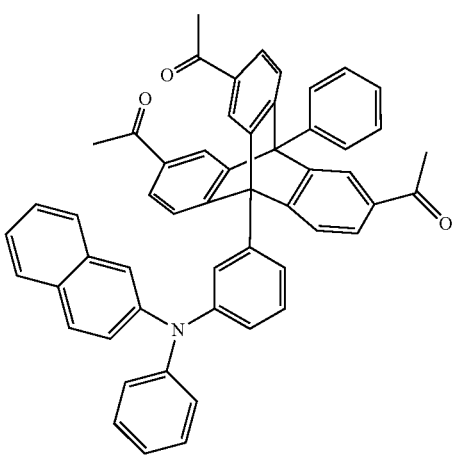

-continued
79
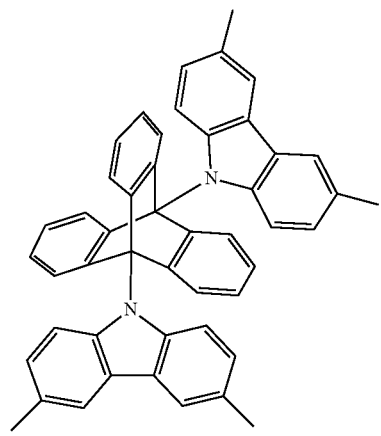
80
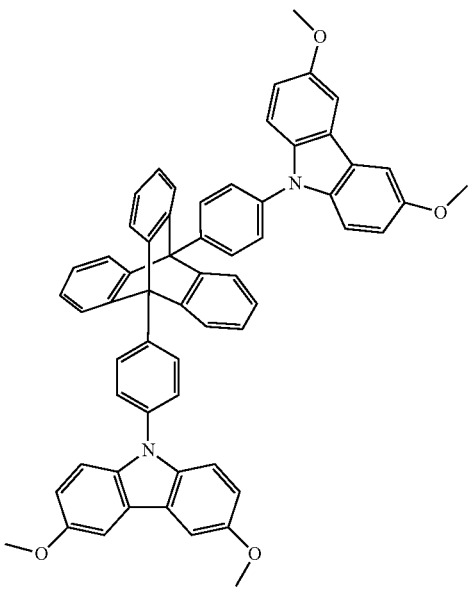
81
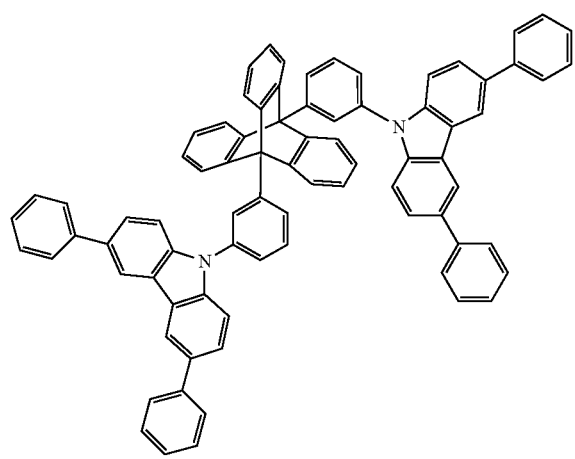
82
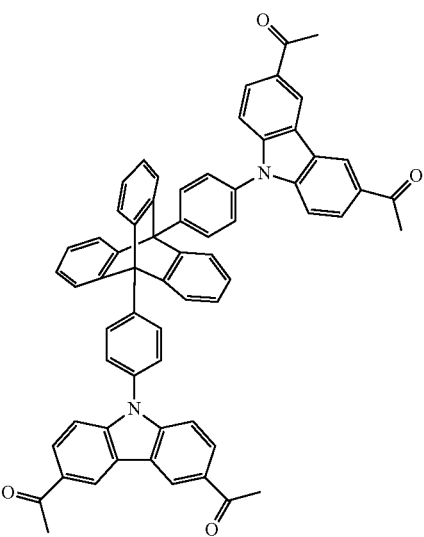
81
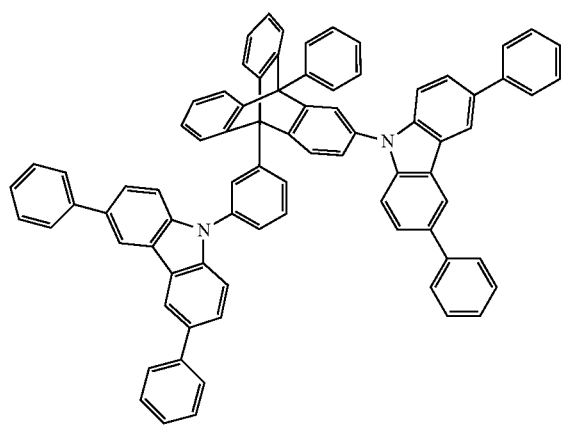

-continued
83
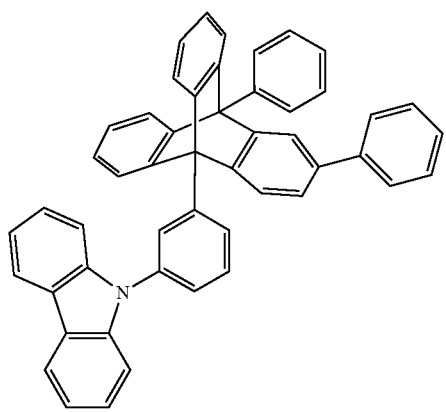
84
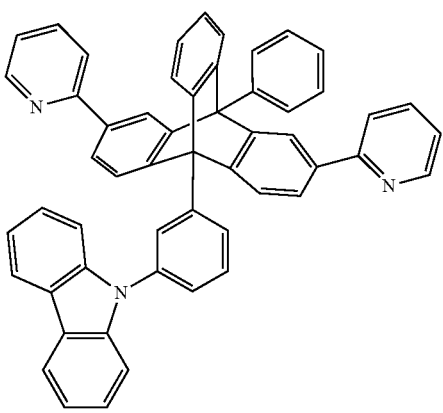
85
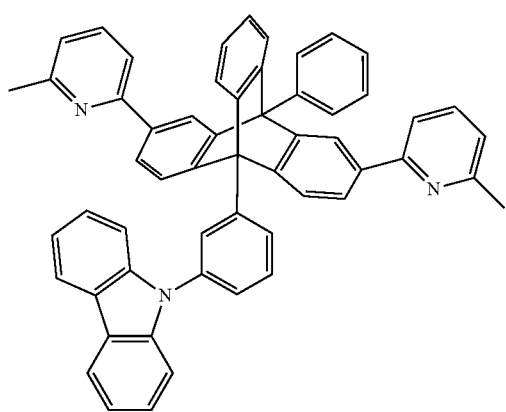
86
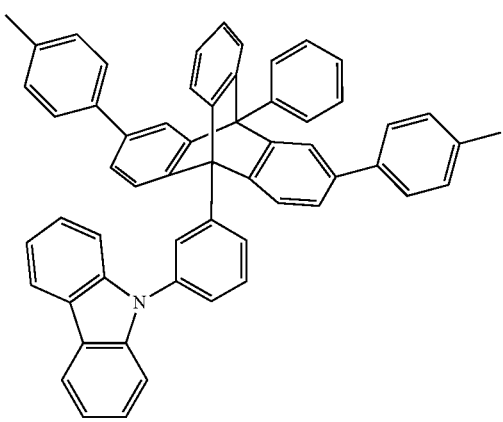
87
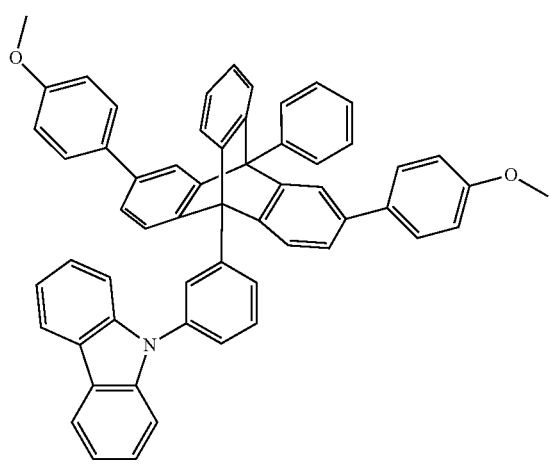
88
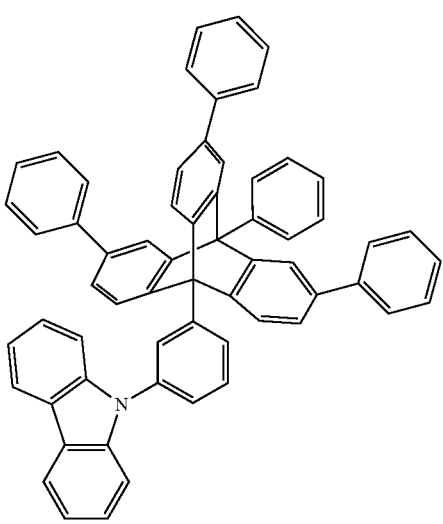

-continued
89
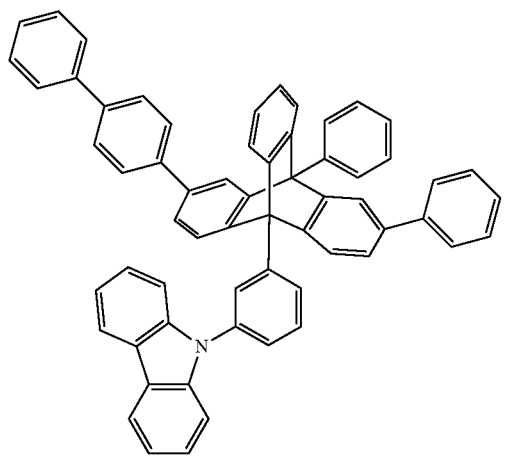
90
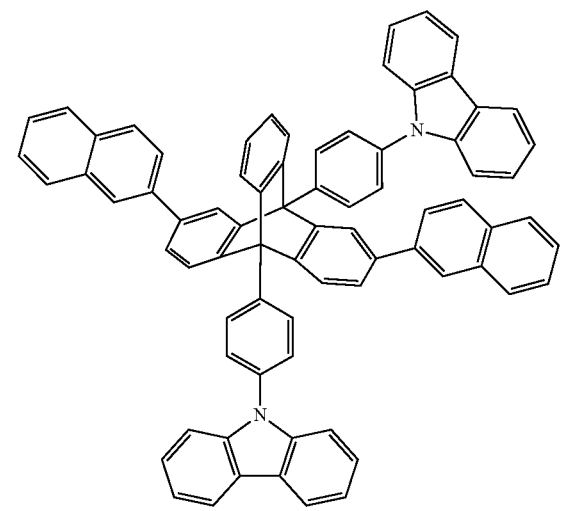
91
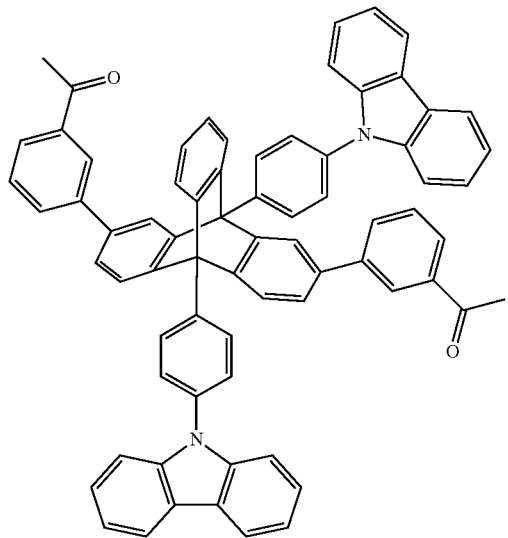
92
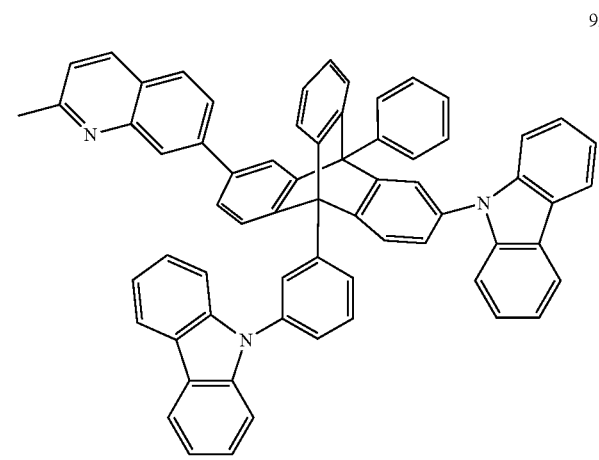
93
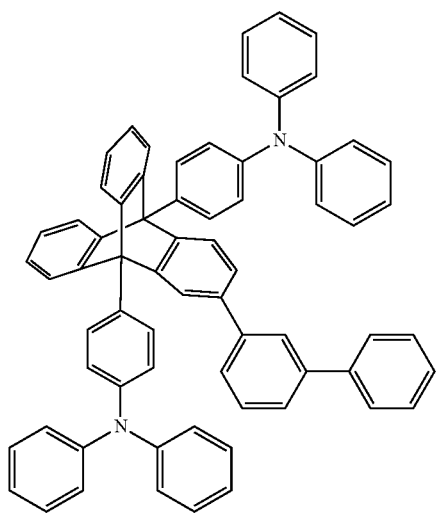
94
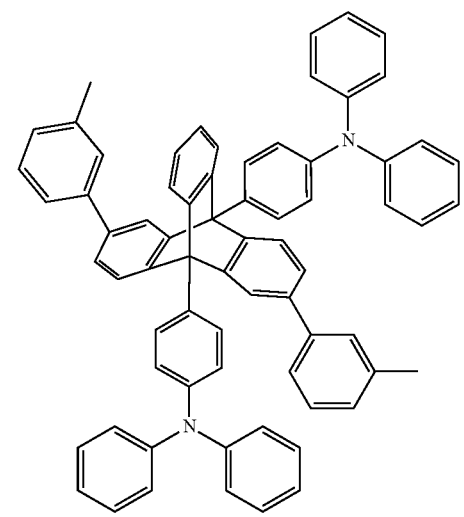

-continued

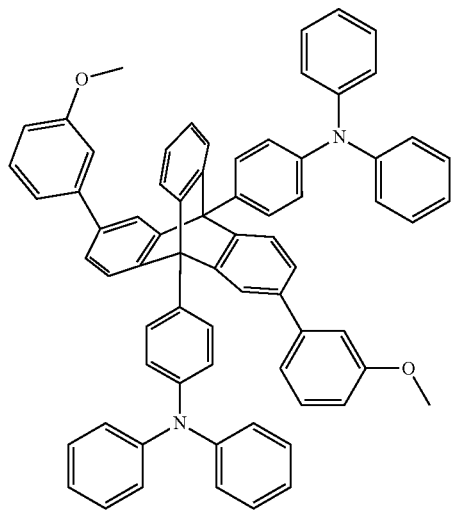

95

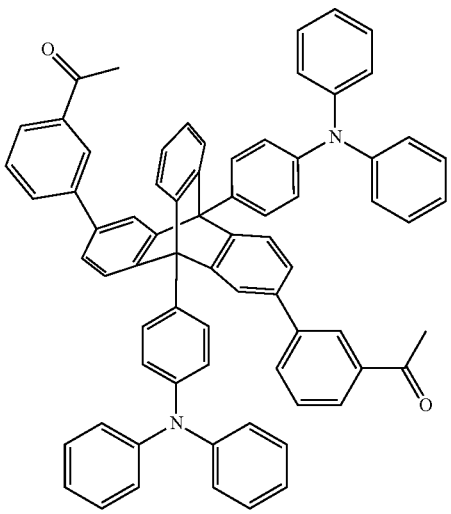

96

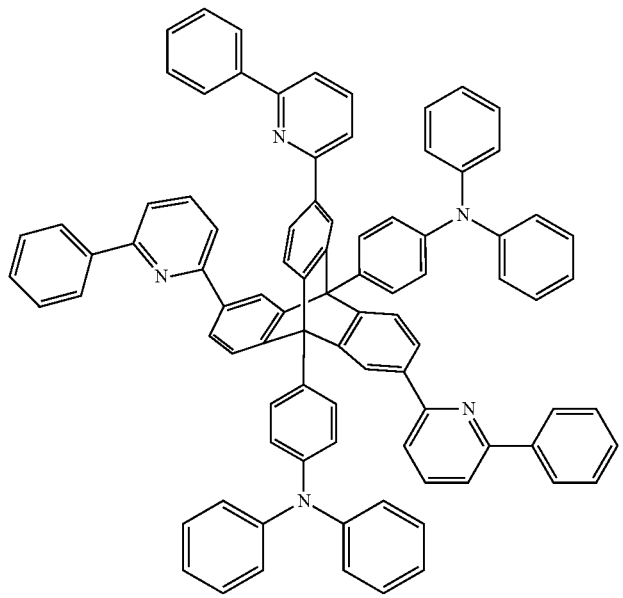

97

The organic EL device of this invention has organic layers containing a light-emitting layer between an anode and a cathode piled one upon another on a substrate. The light-emitting layer here is a phosphorescent light-emitting layer. The organic EL device of this invention contains the aforementioned triptycene derivative in a light-emitting layer, a hole-transporting layer, an electron-blocking layer, or an exciton-blocking layer. The triptycene derivative is preferably contained in a light-emitting layer. More preferably, the triptycene derivative is contained as a host material in a light-emitting layer containing a phosphorescent dopant.

The structure of the organic EL device of this invention will be explained below with reference to the drawing, but it will not be limited to the one illustrated in the drawing.

FIG. 1 schematically shows an example of the structure of an organic EL device generally used in this invention and the symbols in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may contain an exciton-blocking layer adjoining the light-emitting layer or an electron-blocking layer between the light-emitting layer and the hole-injecting layer. The exciton-blocking layer may be disposed either on the anode side or the cathode side of the light-emitting layer and both layers may be disposed simultaneously.

The organic EL device of this invention contains a substrate, an anode, a light-emitting layer, and a cathode as essential layers; in addition, the device preferably contains a hole-injecting/transporting layer and an electron-injecting/transporting layer and further contains a hole-blocking layer between the light-emitting layer and the electron-injecting/transporting layer. The term hole-injecting/transporting layer means a hole-injecting layer and/or a hole-transporting layer while the term electron-injecting/transporting layer means an electron-injecting layer and/or an electron-transporting layer.

It is possible to build a structure that is the reverse of the structure shown in FIG. 1 by piling the cathode 7, the electron-transporting layer 6, the light-emitting layer 5, the hole-transporting layer 4, and the cathode 2 one upon another in this order on the substrate 1. In this case, it is also possible to add or omit a layer or layers according to the need.

—Substrate—

The organic EL device of this invention is preferably supported by a substrate. There is no specific restriction on the substrate and any of the substrates commonly used in organic EL devices can be used. For example, a material for the substrate is selected from glass, transparent plastics, quartz, and the like.

—Anode—

An anode made from an electrode material such as a metal of high work function (4 eV or higher), an alloy, an electrically conductive compound, and a mixture thereof is preferably used in an organic EL device. Examples of the electrode materials of this include electrically conductive transparent materials such as Au and other metals, CuI, indium tin oxide (ITO), $SnO_2$, and ZnO. Further, it is allowable to use an amorphous material such as IDIXO ($In_2O_3$—ZnO) which is capable of forming a transparent electrically conductive film. The anode can be formed by preparing a thin film from any of these electrode materials by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode material. In the case where a material applicable by coating such as an electrically conductive organic compound is used, a wet process such as printing and coating may be employed. In take out of light from the anode, the transmittance is preferably 10% or more and the sheet resistance as an anode is preferably several hundreds Ω/□ or less. Moreover, the thickness of the film is normally in the range of 10-1,000 nm, preferably in the range of 10-200 nm, although it varies with the material used for the film.

—Cathode—

A cathode made from an electrode material such as a metal of low work function (4 eV or lower) (hereinafter referred to as electron-injecting metal), an alloy, an electrically conductive compound, and a mixture thereof is used. Examples of the electrode materials of this kind include sodium, sodium-potassium alloys, magnesium, lithium, magnesium/copper mixtures, magnesium/silver mixtures, magnesium/aluminum mixtures, magnesium/indium mixtures, aluminum/aluminum oxide ($Al_2O_3$) mixtures, indium, lithium/aluminum mixtures, and rare-earth metals. From the viewpoint of electron-injecting property and durability against oxidation, a mixture of an electron-injecting metal and a second metal which is higher in work function and more stable than the electron-injecting metal is suitable for an electrode material and examples include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by forming a thin film of any of these electrode materials by a method such as vapor deposition and sputtering. The sheet resistance as a cathode is preferably several hundred Ω/□ or less and the thickness of the film is selected normally from the range of 10 nm to 5 μm, preferably from the range of 50-200 nm. At least one of the anode and the cathode of an organic EL device is advantageously rendered transparent or translucent to transmit the emitted light and improve the luminance.

The electrically conductive transparent material described earlier in explanation of the anode can be used in the cathode and application of this material makes it possible to fabricate a device in which both anode and cathode display a good transmittance property.

—Light-emitting Layer—

The light-emitting layer is a phosphorescent light-emitting layer and contains a phosphorescent dopant and a host material. A material of preference for the phosphorescent dopant is an organic metal complex containing at least one metal selected from ruthenium, rhodium, palladium, silver, rhenium, osmium, iridium, platinum, and gold. Such organic metal complexes are known in the aforementioned prior-art technical documents and a suitable compound may be selected from them and used.

Preferable examples of the phosphorescent dopants include complexes containing a noble metal element such as Ir in the center, typically Ir(ppy)3, complexes such as Ir(bt)2·acac3, and complexes such as PtOEt3. Examples of these complexes are shown below, but are not limited thereto.

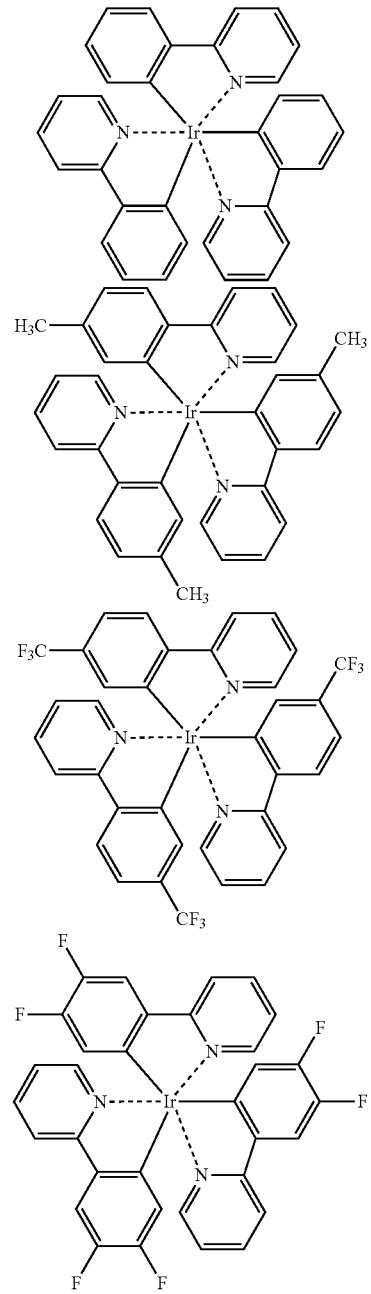

-continued
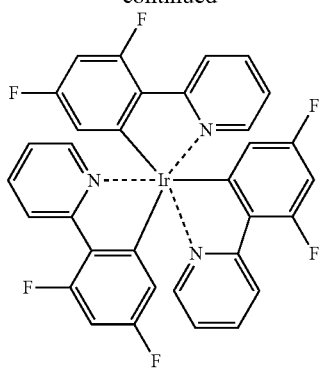
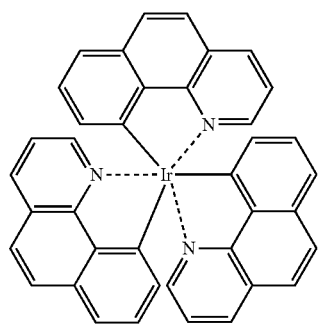
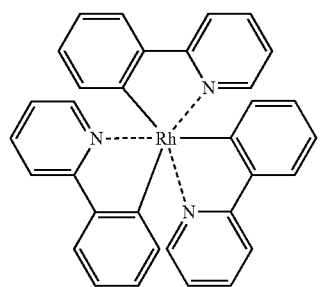
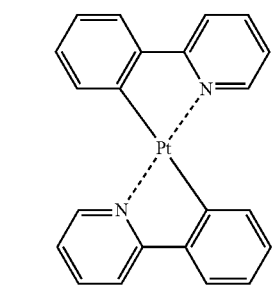
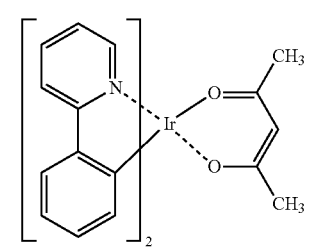
-continued
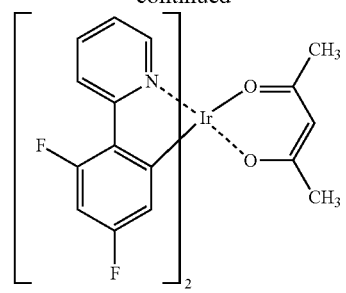
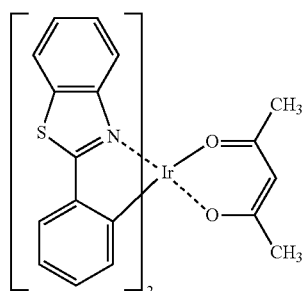
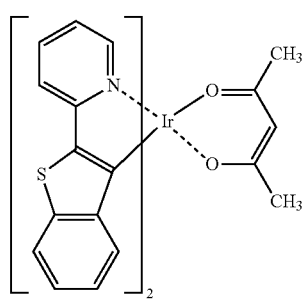
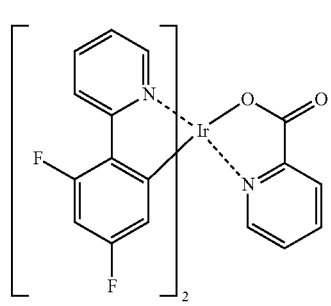
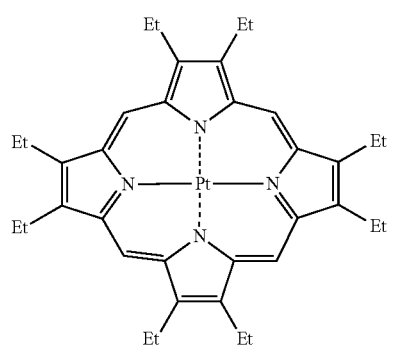

-continued

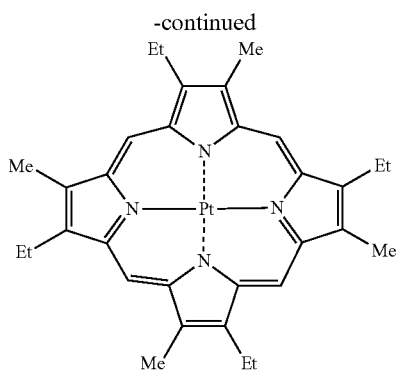

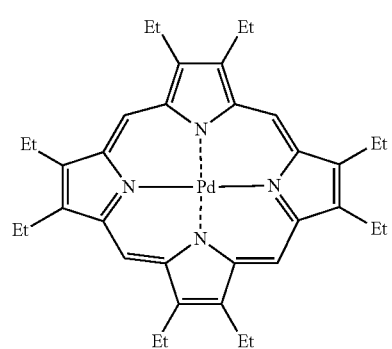

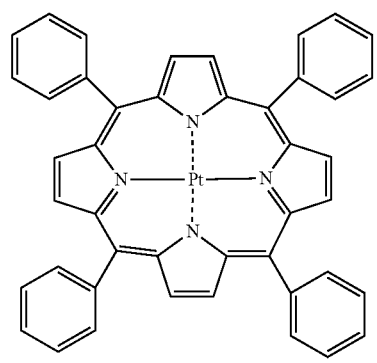

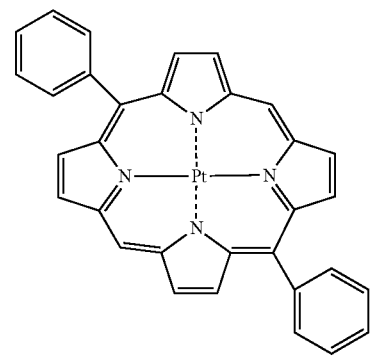

-continued

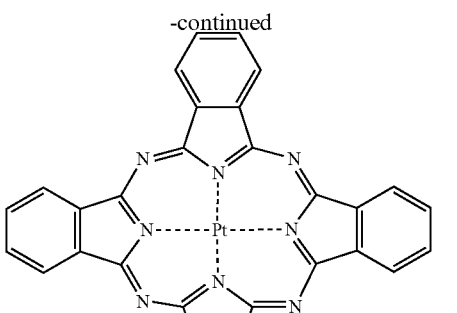

The content of the phosphorescent dopant in the light-emitting layer is in the range of 3-20 wt %, preferably in the range of 5-10 wt %.

A triptycene derivative represented by general formula (1) is preferably used as a host material in the light-emitting layer. However, in the case where the said triptycene derivative is used in any of the organic layers other than the light-emitting layer, a host material of another kind may be used in the light-emitting layer. Further, a triptycene derivative may be used together with a host material of another kind. Still further, a triptycene derivative may be used together with a plurality of known host materials.

The aforementioned host material of another kind is preferably a compound which has a hole transport ability and an electron transport ability, prevents the wavelength of emitted light from becoming longer, and shows high glass transition temperature.

The host materials of this kind are known in a large number of patent documents and elsewhere and a selection may be made from them. Concretely, examples include, but not limited to, indole derivatives, carbazole derivatives, indolocarbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid dianhydrides such as naphthaleneperylene, phthalocyanine derivatives, a variety of metal complexes represented by metal complexes of 8-quinolinol derivatives, metal phthalocyanines, and metal complexes of benzoxazole derivatives and benzothiazole derivatives, and polymeric compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives.

—Injecting Layer—

The injecting layer refers to a layer disposed between the electrode and the organic layer in order to lower the driving voltage and improve the luminance and consists of a hole-injecting layer and an electron-injecting layer. The former is disposed between the anode and the light-emitting or hole-transporting layer while the latter is disposed between the cathode and the light-emitting or electron-transporting layer. The injecting layers may be provided according to the need.

—Hole-blocking Layer—

The hole-blocking layer in a broad sense has a function of an electron-transporting layer and it is composed of a hole-blocking material which retains a function of transporting electrons while displaying a markedly reduced ability to transport holes. Thus, the hole-blocking layer can improve the probability of recombination of electrons and holes by transporting electrons while blocking holes. Further, an electron-transporting material useful for the electron-transporting layer to be described later may be used as a material for the hole-blocking layer according to the need.

—Electron-blocking Layer—

The electron-blocking layer is composed of a material which retains a function of transporting holes while displaying a markedly reduced ability to transport electrons and it can improve the probability of recombination of electrons and holes by transporting holes while blocking electrons.

A hole-transporting material useful for the hole-transporting layer to be described later may be used as a material for the electron-blocking layer according to the need. A triptycene derivative represented by general formula (1) is excellent as a material for the electron-blocking layer. However, in the case where a triptycene derivative is used in any one of the organic layers other than the electron-blocking layer, another known electron-blocking material may be used instead. The thickness of the electron-blocking layer is preferably 3-100 nm, more preferably 5-30 nm.

—Exciton-blocking Layer—

The exciton-blocking layer is a layer provided to prevent excitons generated by recombination of holes and electrons in the light-emitting layer from diffusing into the charge-transporting layer and insertion of this layer can confine excitons efficiently in the light-emitting layer to enhance the luminous efficiency of the device. The exciton-blocking layer may be inserted adjoining the light-emitting layer, on the side of the anode or cathode or on both sides.

A hole-transporting material may be used as a material for the exciton-blocking layer according to the need. A triptycene derivative represented by general formula (1) is an excellent exciton-blocking material. However, in the case where a triptycene derivative is used in any one of the organic layers other than the exciton-blocking layer, another known exciton-blocking material may be used instead.

Examples of the known exciton-blocking materials include 1,3-dicarbazolylbenzene (mCP) and bis(2-methyl-8-quinolinolato)-4-phenylphenolatoaluminum(III) (BAlq).

—Hole-transporting Layer—

The hole-transporting layer is composed of a hole-transporting material which has a function of transporting holes and it may be constituted of a single layer or multiple layers.

The hole-transporting material has a function of injecting or transporting holes or acting as a barrier to electrons. A triptycene derivative represented by general formula (1) is a hole-transporting material and is excellent as such. However, in the case where a triptycene derivative is used in any one of the organic layers other than the hole-transporting layer, another known hole-transporting material may be used instead.

Examples of the hole-transporting materials include triazole derivatives, oxadiazole derivatives, imidazole derivatives, polyarylalkane derivatives, pyrazoline and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electrically conductive oligomers, particularly thiophene oligomers. Porphyrin compounds, aromatic tertiary amine compounds, and styrylamine compounds are used preferably and aromatic tertiary amine compounds are used more preferably.

—Electron-transporting Layer—

The electron-transporting layer is composed of an electron-transporting material which has a function of transporting electrons and it may be constituted of a single layer or multiple layers.

An electron-transporting material for the electron-transporting layer is of use as long as it has a function of transporting electrons injected from the cathode to the light-emitting layer and it may be arbitrarily selected from the known compounds; for example, nitro-substituted fluorene derivatives, diphenylquinone derivatives, thiopyran dioxide derivatives, carbodiimides, fluorenylidenemethane derivatives, anthraquinodimethan and anthrone derivatives, and oxadiazole derivatives. Further, thiadiazole derivatives which are derived from oxadiazole derivatives by substituting the oxygen atom in the ring with a sulfur atom and quinoxaline derivatives whose quinoxaline ring is known as an electron-withdrawing group are useful as electron-transporting materials. Still further, polymeric materials which contain the aforementioned materials in the polymer chain or as the polymer backbone are also useful.

The organic EL device of this invention may contain a hole-blocking layer. In this case, a material to be used for the hole-blocking layer is selected from the aforementioned electron-transporting materials.

A triptycene derivative represented by general formula (1) is an excellent hole-transporting material and it is preferably incorporated in the light-emitting layer, the hole-transporting layer, the electron-blocking layer, or the exciton-blocking layer.

The organic EL device of this invention is applicable to a single device, a device with its structure arranged in array, or a device in which the anode and the cathode are arranged in X-Y matrix. As the organic EL device of this invention utilizes emission of light by phosphorescence, it performs at higher luminous efficiency with much more improved driving stability than the conventional devices utilizing emission of light from the excited singlet state and displays excellent performance when applied to full-color or multicolor panels.

EXAMPLES

This invention will be explained in more detail below with reference to the examples; however, this invention will not be limited to these examples.

The synthesis of triptycene derivatives was carried out according to the routes illustrated below. The compound number corresponds to the number assigned to the chemical formula shown earlier in the specification.

Example 1

Synthesis of Compound 3

In a 2,000-ml three-necked flask were placed 20 g (59.5 mmol) of 9,10-dibromoanthracene, 20 g (143 mmol) of 3-fluorophenylboronic acid, and 5 g (4.32 mmol) of tetrakis(triphenylphosphine)palladium(0), then 500 ml of ethanol and 600 ml of toluene were added, and the mixture was stirred. A solution of 21.6 g (203.7 mmol) of sodium carbonate in 300 ml of water was then thrown into the flask. Thereafter, the mixture was heated to 100° C. and stirred for 17 hours. The reaction solution was cooled to room temperature, transferred to a 2,000-ml separatory funnel, and separated into an organic layer and an aqueous layer. The organic layer was washed twice with 200 ml of water, then dehydrated over magnesium sulfate, the magnesium sulfate was filtered off, and the solvent was distilled off under reduced pressure. The reaction product thus obtained was then reslurried in 300 ml of methanol to yield 21 g of Intermediate (I) as a white solid.

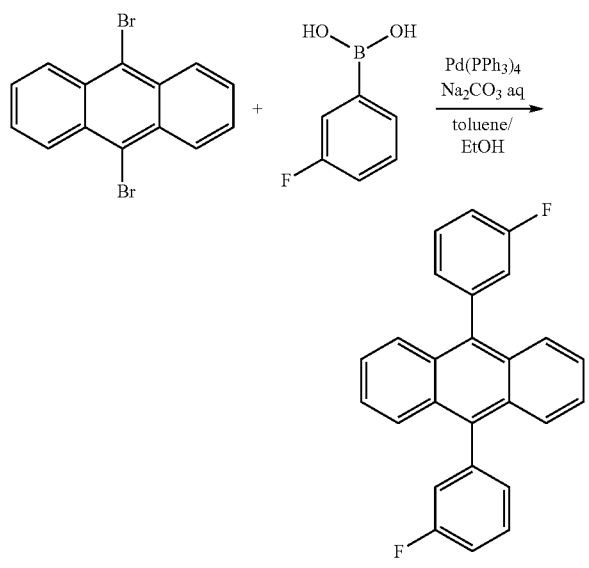

Under a nitrogen atmosphere, 21 g (57.3 mmol) of Intermediate (I) and 300 ml of 1,2-dichloroethane were introduced into a 1,000-ml three-necked flask and the mixture was stirred at 80° C. until a solution resulted. To the flask was added 43.3 ml (326 mmol) of isoamyl nitrite and the mixture was stirred at 80° C. for 5 minutes. Then, a solution of 43.4 g (316.4 mmol) of anthranilic acid in 300 ml of diethylene glycol dimethyl ether was added dropwise and the mixture was stirred at 150° C. for 2 hours. The 1,2-dichloroethane was then removed by distillation. The remainder was cooled to room temperature, added to a solution of 20 g of potassium hydroxide in a mixture of 200 ml of water and 800 ml of methanol, the mixture was stirred at 0° C. for 2 hours, and the separated solid was collected by filtration. The reaction mixture thus obtained was purified by silica gel column chromatography to yield 6.2 g of Intermediate (II) as a white solid.

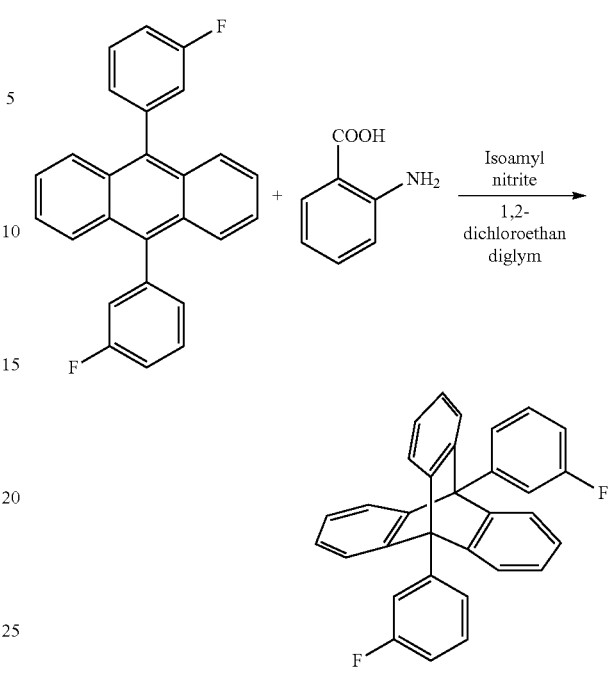

In a 200-ml three-necked flask were placed 5.4 g (131 mmol) of sodium hydride (58.3% dispersion) and 20 ml of anhydrous DMF and stirred under nitrogen flow. To the resulting suspension was added a solution of 18.9 g (113 mmol) of carbazole in 40 ml of anhydrous DMF. The mixture was stirred at room temperature for 30 minutes, then a solution of 5.4 g of Intermediate (II) in 50 ml of anhydrous DMF was added, and the mixture was stirred at 140° C. for 66 hours. Thereafter, the mixture was cooled to room temperature, 50 ml of methanol and 200 ml of water were added, and the separated solid was collected by filtration. The solid was washed by dispersing in methanol with application of heat and then reslurried in ethyl acetate with application of heat. The white solid thus obtained was dried by heating under reduced pressure to yield 4 g of Compound 3: EI-MS, 737 (M+1); glass transition temperature, 169° C.

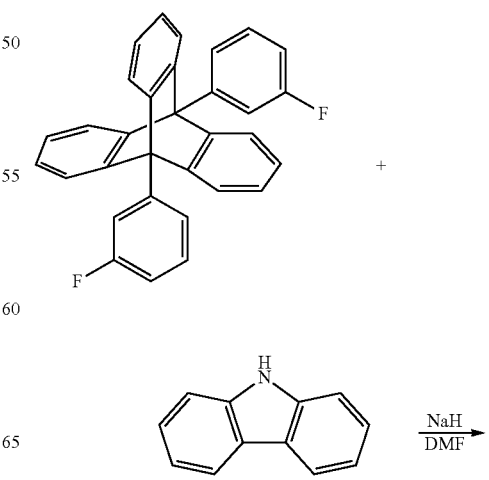

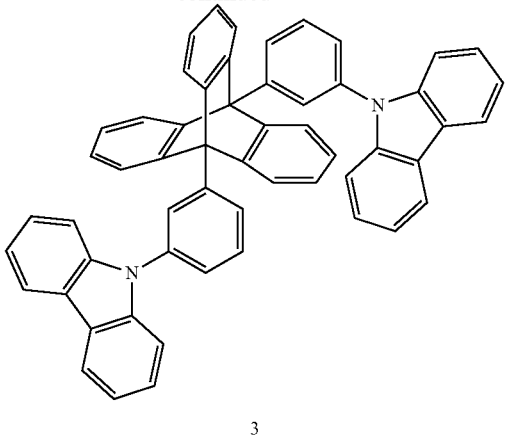

3

Example 2

Synthesis of Compound 7

In a 2,000-ml three-necked flask were placed 25 g (74.4 mmol) of 9,10-dibromoanthracene, 22 g (180 mmol) of phenylboronic acid, and 5 g (4.32 mmol) of tetrakis(triphenylphosphine)palladium(0), then 400 ml of ethanol and 600 ml of toluene were added, and the mixture was stirred. Then, a solution of 27 g (254.7 mmol) of sodium carbonate in 250 ml of water was thrown into the flask and the mixture was heated to 90° C. and stirred for 18 hours. The reaction solution was cooled to room temperature, transferred to a 2,000-ml separatory funnel, and separated into an organic layer and an aqueous layer. The organic layer was washed twice with 200 ml of water, then dehydrated over magnesium sulfate, the magnesium sulfate was filtered off, and the solvent was distilled off under reduced pressure. The reaction product thus obtained was then reslurried in 200 ml of ethyl acetate to yield 23 g of Intermediate (III) as a white solid.

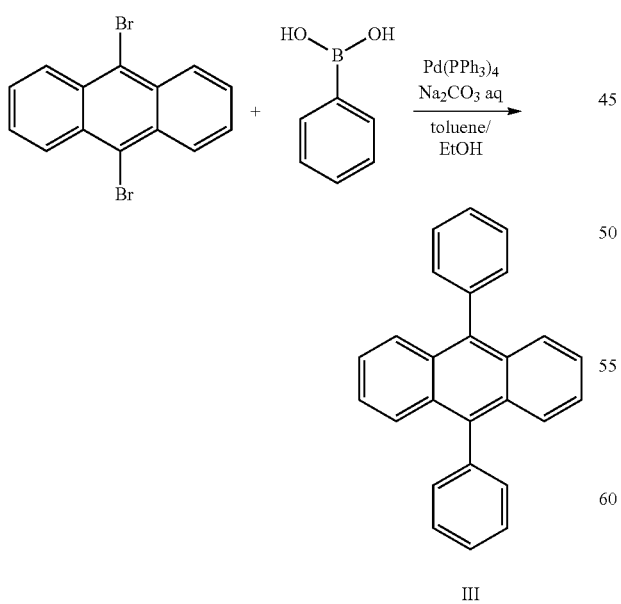

III

Under a nitrogen atmosphere, 22 g (66.6 mmol) of Intermediate (III) and 180 ml of 1,2-dichloroethane were introduced into a 1,000-ml three-necked flask and the mixture was stirred at 80° C. until a solution resulted. Then, 20 ml (150.2 mmol) of isoamyl nitrite was added and the mixture was stirred at 80° C. for 5 minutes. A solution of 25 g (115.7 mmol) of anthranilic acid in 100 ml of diethylene glycol dimethyl ether was added dropwise and the mixture was stirred at 150° C. for 3 hours. The reaction mixture was cooled to room temperature, purified by silica gel column chromatography, and then reslurried in chloroform with application of heat to yield 6.5 g of Intermediate (IV).

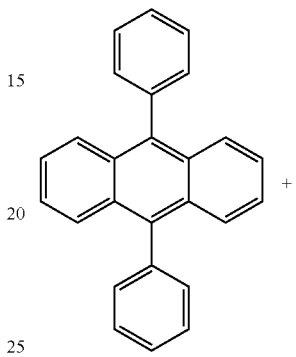

+

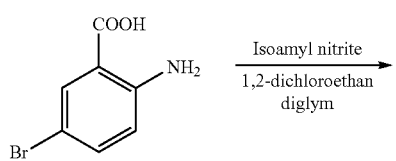

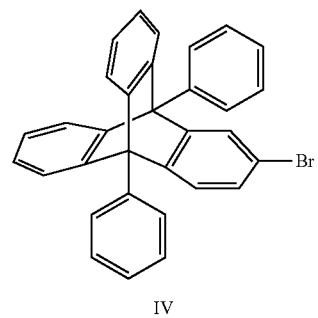

IV

Under a nitrogen atmosphere, 6.5 g (13.4 mmol) of Intermediate (IV), 2.7 g (16.1 mmol) of carbazole, 3.0 g (15.8 mmol) of copper(I) iodide, and 3.7 g (26.8 mmol) of potassium carbonate were introduced into a 200-ml three-necked flask, then 100 ml of quinoline was added, and the mixture was heated at 170° C. for 30 hours with stirring. The reaction mixture was cooled to room temperature, 100 ml of dichloromethane and 50 ml of water were added, and the mixture was stirred for 1 hour, then transferred to a 500-ml separatory funnel, and separated into an organic layer and an aqueous layer. The organic layer was washed twice with 200 ml of water, then dehydrated over magnesium sulfate, the magnesium sulfate was filtered off, and the solvent was distilled off under reduced pressure. The reaction mixture thus obtained was purified by silica gel column chromatography and then reslurried in ethyl acetate with application of heat to yield 4.6 g of Compound 7 as a white solid.

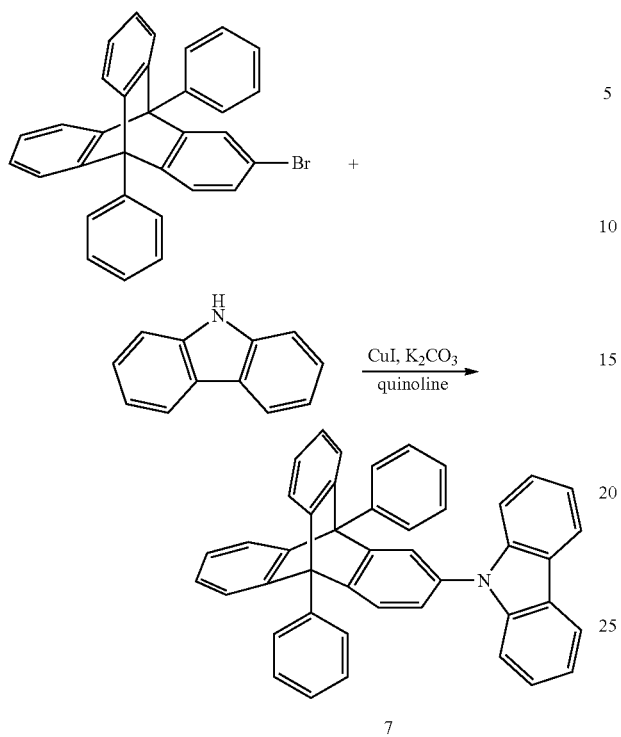

Example 3

Synthesis of Compound 16

In a 500-ml three-necked flask were placed 6.9 g (14.2 mmol) of Intermediate (IV), 4.88 g (17 mmol) of 3-carbazolylphenylboronic acid, and 1 g (0.86 mmol) of tetrakis(triphenylphosphine)palladium(0), then 100 ml of ethanol and 200 ml of toluene were added, and the mixture was stirred. Then, a solution of 4.5 g (42.5 mmol) of sodium carbonate in 50 ml of water was thrown into the flask and the mixture was heated to 90° C. and stirred for 3 hours. The reaction solution was cooled to room temperature, transferred to a 1,000-ml separatory funnel, and separated into an organic layer and an aqueous layer. The organic layer was washed twice with 200 ml of water, then dehydrated over magnesium sulfate, the magnesium sulfate was filtered off, and the solvent was distilled off under reduced pressure. The reaction mixture thus obtained was purified by silica gel column chromatography and then reslurried in methanol to yield 5.4 g of Compound 16.

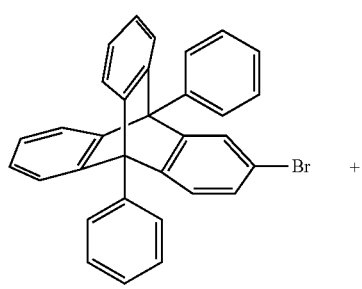

Example 4

An organic EL device was fabricated by piling the constituent layers in thin film one upon another on a glass substrate on which a 110 nm-thick indium tin oxide (ITO) anode had been formed while applying the vapor deposition process at a degree of vacuum of $4.0 \times 10^{-4}$ Pa. First, a hole-injecting layer was formed by depositing copper phthalocyanine (CuPC) on the ITO anode to a thickness of 30 nm. Then, a hole-transporting layer was formed by depositing N,N'-di(naphthalen-1-yl)-N,N'-diphenylbenzidine (NPB) to a thickness of 80 nm. A light-emitting layer was then formed by co-depositing Compound 3 as a host material and bis[2-(4,6-difluorophenyl)pyridinato-N,C2']iridium picolinate (Flrpic), a phosphorescent blue light-emitting material, as a dopant from different evaporation sources on the hole-transporting layer to a thickness of 35 nm. The concentration of Flrpic was 8.0%. An electron-transporting layer was then formed by depositing Alq3 to a thickness of 25 nm. Further, an electron-injecting layer was formed by depositing lithium fluoride (LiF) on the electron-transporting layer to a thickness of 0.5 nm. Finally, an electrode was formed by depositing aluminum (Al) on the electron-injecting layer to a thickness of 170 nm. The organic EL device thus fabricated has the layered structure illustrated in FIG. 1 to which the electron-injecting layer is added between the cathode and the electron-transporting layer.

The organic EL device was connected to an outside power source and, when direct current voltage was applied, the device was confirmed to emit light with the characteristics shown in Table 1. In Table 1, the luminance, voltage, and luminous efficiency were measured at 2.5 mA/cm². The maximum wavelength of the spectrum of light emitted from the device was 470 nm and this indicates that light is emitted from Flrpic.

Example 5

An organic EL device was fabricated as in Example 4 with the exception of using Compound 7 as a host material in the light-emitting layer.

Example 6

An organic EL device was fabricated as in Example 4 with the exception of using Compound 16 as a host material in the light-emitting layer.

Example 7

An organic EL device was fabricated as in Example 4 with the exception of using Compound 28 as a host material in the light-emitting layer.

Example 8

An organic EL device was fabricated as in Example 4 with the exception of using Compound 43 as a host material in the light-emitting layer.

Example 9

An organic EL device was fabricated as in Example 4 with the exception of using Compound 47 as a host material in the light-emitting layer.

Comparative Example 1

An organic EL device was fabricated as in Example 4 with the exception of using mCP as a host material in the light-emitting layer.

Comparative Example 2

An organic EL device was fabricated as in Example 4 with the exception of using 9,10-diphenyltriptycene as a host material in the light-emitting layer.

Comparative Example 3

An organic EL device was fabricated as in Example 4 with the exception of using 2-carbazolyltriptycene as a host material in the light-emitting layer.

The maximum wavelength of the spectrum of light emitted from each of the organic EL devices fabricated in Examples 4-9 and Comparative Examples 1-3 is 470 nm and it was acknowledged that light is emitted from FIrpic in each case. The luminous characteristics are shown in Table 1.

TABLE 1

|  | Luminance (cd/m$^2$) | Voltage | Luminous efficiency |
|---|---|---|---|
| Example 4 | 372 | 9.8 | 4.6 |
| 5 | 289 | 10.6 | 3.4 |
| 6 | 298 | 11.1 | 3.3 |
| 7 | 371 | 9.7 | 4.8 |
| 8 | 274 | 11.2 | 3.1 |
| 9 | 266 | 10.6 | 3.0 |
| Comparative example 1 | 242 | 10.9 | 2.8 |
| 2 | 145 | 10.1 | 2.0 |
| 3 | 175 | 10.8 | 2.1 |

Example 10

An organic EL device was fabricated by piling the constituent layers in thin film one upon another on a glass substrate on which a 150 nm-thick indium tin oxide (ITO) anode had been formed while applying the vapor deposition process at a degree of vacuum of $4.0 \times 10^{-4}$ Pa. First, a hole-transporting layer was formed by depositing NPB on the ITO anode to a thickness of 60 nm. A light-emitting layer was then formed by co-depositing Compound 3 and Ir(ppy)3 from different evaporation sources on the hole-transporting layer to a thickness of 25 nm. The concentration of Ir(ppy)3 at this point was 7.0 wt %. After this, an electron-transporting layer was formed by depositing Alq3 to a thickness of 50 nm. Further, an electron-injecting layer was formed by depositing lithium fluoride (LiF) on the electron-transporting layer to a thickness of 0.5 nm. Finally, an electrode was formed by depositing aluminum (Al) on the electron-injecting layer to a thickness of 170 nm.

The organic EL device thus fabricated was connected to an outside power source and, when direct current voltage was applied, it displayed the luminous characteristics shown in Table 2. In Table 2, the luminance, voltage, and luminous efficiency were measured at 2.5 mA/cm$^2$.

Example 11

An organic EL device was fabricated as in Example 10 with the exception of using Compound 7 as a host material in the light-emitting layer.

Example 12

An organic EL device was fabricated as in Example 10 with the exception of using Compound 16 as a host material in the light-emitting layer.

Example 13

An organic EL device was fabricated as in Example 10 with the exception of using Compound 28 as a host material in the light-emitting layer.

Example 14

An organic EL device was fabricated as in Example 10 with the exception of using Compound 43 as a host material in the light-emitting layer.

Example 15

An organic EL device was fabricated as in Example 10 with the exception of using Compound 47 as a host material in the light-emitting layer.

Comparative Example 4

An organic EL device was fabricated as in Example 10 with the exception of using CBP as a host material in the light-emitting layer.

Comparative Example 5

An organic EL device was fabricated as in Example 10 with the exception of using 9,10-diphenyltriptycene as a host material in the light-emitting layer.

Comparative Example 6

An organic EL device was fabricated as in Example 10 with the exception of using 2-carbazolyltriptycene as a host material in the light-emitting layer.

The maximum wavelength of the spectrum of light emitted from each of the organic EL devices fabricated in Examples 10-15 and Comparative Examples 4-6 is 517 nm and it was acknowledged that light is emitted from Ir(ppy)3 in each case. The luminous characteristics are shown in Table 2.

TABLE 2

|  | Luminance (cd/m$^2$) | Voltage (V) | Luminous efficiency (lm/W) |
| --- | --- | --- | --- |
| Example 10 | 1502 | 6.9 | 26.4 |
| 11 | 1152 | 7.2 | 20.3 |
| 12 | 1254 | 6.4 | 25.1 |
| 13 | 1576 | 6.3 | 27.6 |
| 14 | 997 | 7.1 | 17.4 |
| 15 | 980 | 7.0 | 17.0 |
| Comparative example 4 | 824 | 7.1 | 14.5 |
| 5 | 338 | 7.0 | 5.8 |
| 6 | 428 | 7.2 | 7.5 |

Example 16

An organic EL device was fabricated by piling the constituent layers in thin film one upon another on a glass substrate on which a 150 nm-thick indium tin oxide (ITO) anode had been formed while applying the vapor deposition process at a degree of vacuum of 4.0×10$^{-4}$ Pa. First, a hole-transporting layer was formed by depositing Compound 3 on the ITO anode to a thickness of 60 nm. Then, a light-emitting layer was formed by co-depositing CBP and Ir(ppy)3 from different evaporation sources on the hole-transporting layer to a thickness of 25 nm. The concentration of Ir(ppy)3 at this point was 7.0 wt %. After this, an electron-transporting layer was formed by depositing Alq3 to a thickness of 50 nm. Further, an electron-injecting layer was formed by depositing lithium fluoride (LiF) on the electron-transporting layer to a thickness of 0.5 nm. Finally, an electrode was formed by depositing aluminum (Al) on the electron-injecting layer to a thickness of 170 nm.

The organic EL device thus fabricated was connected to an outside power source and, when direct current voltage was applied, it displayed the luminous characteristics shown in Table 3. In Table 3, the luminance, voltage, and luminous efficiency were measured at 2.5 mA/cm$^2$. The maximum wavelength of the spectrum of light emitted from the device was 517 nm and this indicates that light is emitted from Ir(ppy)3.

Example 17

An organic EL device was fabricated as in Example 16 with the exception of using Compound 43 as a hole-transporting material.

Example 18

An organic EL device was fabricated as in Example 16 with the exception of using Compound 47 as a hole-transporting material.

The maximum wavelength of the spectrum of light emitted from each of the organic EL devices fabricated in Examples 16-18 is 517 nm and this indicates that light is emitted from Ir(ppy)3 in each case. The luminous characteristics are shown in Table 3. It is seen that the characteristics of these devices are better than those of the organic EL device fabricated in Comparative Example 4.

TABLE 3

|  | Luminance (cd/m$^2$) | Voltage (V) | Luminous efficiency (lm/W) |
| --- | --- | --- | --- |
| Example 16 | 1739 | 6.3 | 33.4 |
| 17 | 1988 | 7.0 | 35.0 |
| 18 | 1590 | 7.1 | 27.8 |

Example 19

An organic EL device was fabricated by piling the constituent layers in thin film one upon another on a glass substrate on which a 150 nm-thick indium tin oxide (ITO) anode had been formed while applying the vapor deposition process at a degree of vacuum of 4.0×10$^{-4}$ Pa. First, a hole-transporting layer was formed by depositing NPB on the ITO anode to a thickness of 50 nm. Then, an electron-blocking layer was formed by depositing Compound 3 on the hole-transporting layer to a thickness of 10 nm. A light-emitting layer was then formed by co-depositing CBP and Ir(ppy)3 from different evaporation sources to a thickness of 25 nm. The concentration of Ir(ppy)3 at this point was 7.0 wt %. After this, an electron-transporting layer was formed by depositing Alq3 to a thickness of 50 nm. Further, an electron-injecting layer was formed by depositing lithium fluoride (LiF) on the electron-transporting layer to a thickness of 0.5 nm. Finally, an electrode was formed by depositing aluminum (Al) on the electron-injecting layer to a thickness of 170 nm.

The organic EL device thus fabricated was connected to an outside power source and, when direct current voltage was applied, the device was confirmed to display the luminous characteristics shown in Table 4. In Table 4, the luminance, voltage, and luminous efficiency were measured at 2.5 mA/cm$^2$. The maximum wavelength of the spectrum of light emitted from the device was 517 nm and this indicates that light is emitted from Ir(ppy)3.

Example 20

An organic EL device was fabricated as in Example 19 with the exception of using Compound 43 as an electron-blocking material.

Example 21

An organic EL device was fabricated as in Example 19 with the exception of using Compound 47 as an electron-blocking material.

The maximum wavelength of the spectrum of light emitted from each of the organic EL devices fabricated in Examples 19-21 is 517 nm and this indicates that light is emitted from Ir(ppy)3 in each case. The luminous characteristics are shown in Table 4. It is seen that the characteristics of these devices are better than those of the organic EL device fabricated in Comparative Example 4.

TABLE 4

|  | Luminance (cd/m$^2$) | Voltage (V) | Luminous efficiency (lm/W) |
| --- | --- | --- | --- |
| Example 19 | 1589 | 6.7 | 30.6 |
| 20 | 1831 | 7.3 | 32.2 |
| 21 | 1511 | 7.2 | 26.6 |

Industrial Applicability

The triptycene derivative of this invention for use in an organic electroluminescent device is also called a phosphorescent electroluminescent device material because of its potential use as such. The triptycene derivative shows a good balance of electrical charges due to its good electron injection and hole transport properties and incorporation of this compound in an organic EL device improves the probability of recombination of holes and electrons. Further, the triptycene derivative incorporated in the device can effectively prevent the transfer of the triplet excitation energy from the dopant to the host material because the lowest triplet excitation energy of the triptycene derivative is sufficiently high to confine the lowest triplet excitation energy of the dopant. In addition, the said triptycene derivative shows good characteristics in the amorphous state, high heat stability, and electrochemical stability and, as a result, it enables fabrication of an organic EL device of long lifetime and high durability to become a reality. In particular, placing a hole-transporting substituent at the benzyl position helps to maintain a good balance of electrical charges and extract better characteristics. In addition, a group of compounds possessing the aforementioned characteristics show high glass transition temperature and good heat stability. On account of these properties, the organic EL device of this invention can achieve high luminous efficiency.

The organic EL device of this invention satisfies a level of performance required for practical use in respect to the luminous characteristics, driving life, and durability and is of high technical value because of its potential applicability to flat panel displays (for example, mobile phone display devices, vehicle-mounted display devices, office computer display devices, and television sets), light sources utilizing the characteristics of planar light emitters (for example, illumination, light sources for copiers, and backlight sources for liquid crystal displays and instruments), signboards, and beacon lights.

The invention claimed is:

1. An organic electroluminescent device comprising an anode, organic layers containing a phosphorescent light-emitting layer, and a cathode piled one upon another on a substrate wherein the organic layer of the phosphorescent light-emitting layer comprises a triptycene derivative represented by general formula (1):

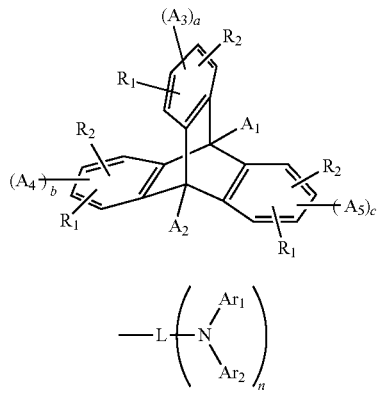

wherein in general formula (1), $A_1$ to $A_5$ each is independently a substituent represented by formula (2);

a, b, and c each is an integer of 0-2 and $0 \leq a+b+c \leq 3$; and $R_1$ and $R_2$ each is independently hydrogen, an alkyl group of 1-10 carbon atoms, an alkoxyl group of 1-6 carbon atoms, or an acyl group of 2-6 carbon atoms;

wherein in formula (2), n is an integer of 0-1 and the sum of n's in general formula (1) is an integer of 1;

L is a group derived from benzene, pyridine, or pyrimidine; and $Ar_1$ and $Ar_2$ each is independently an aromatic hydrocarbon group of 6-18 carbon atoms or an aromatic heterocyclic group of 3-17 carbon atoms, and $Ar_1$, $Ar_2$ and the nitrogen atom together optionally form a nitrogen-containing heterocycle.

2. The organic electroluminescent device as described in claim 1, wherein the substituent represented by formula (2) is a substituent represented by formula (3):

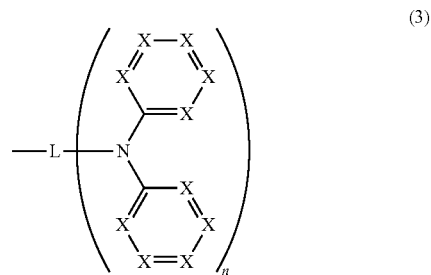

wherein L and n respectively have the same meaning as in formula (2);

X is independently a methine group or nitrogen;

the two aromatic rings bonded to the nitrogen atom are optionally fused to form three rings with a ring containing the said nitrogen atom being located at the center ring.

3. The organic electroluminescent device as described in claim 1, wherein the triptycene derivative represented by general formula (1) is a triptycene derivative represented by general formula (4):

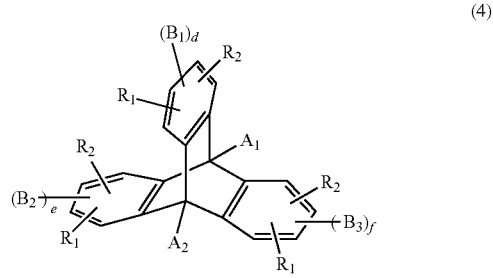

wherein $A_1$, $A_2$, $R_1$, and $R_2$ respectively have the same meaning as in general formula (1); however, the sum of the integers designated as n in formula (2) is 1 in general formula (4);

$B_1$ to $B_3$ each is independently the substituent represented by formula (2), but all the integers designated as n are 0; and d, e, and f each is an integer of 0-2 and $0 \leq d+e+f \leq 3$.

* * * * *